(12) United States Patent
Ertel et al.

(10) Patent No.: US 12,007,345 B2
(45) Date of Patent: Jun. 11, 2024

(54) DIELECTRIC SPECTROSCOPY SENSING APPARATUS AND METHOD OF USE

(71) Applicant: XaTek, Inc., Chagrin Falls, OH (US)

(72) Inventors: Jason R. Ertel, Twinsburg, OH (US); Shawn Dellinger, Cleveland, OH (US); Jason Grant Tilk, Cleveland Hts., OH (US); David J. Boll, Avon, OH (US)

(73) Assignee: XaTek, Inc., Chagrin Falls, OH (US)

( * ) Notice: Subject to any disclaimer, the term of this patent is extended or adjusted under 35 U.S.C. 154(b) by 406 days.

(21) Appl. No.: 17/294,536

(22) PCT Filed: Nov. 15, 2019

(86) PCT No.: PCT/US2019/061613
§ 371 (c)(1),
(2) Date: May 17, 2021

(87) PCT Pub. No.: WO2020/106556
PCT Pub. Date: May 28, 2020

(65) Prior Publication Data
US 2022/0065805 A1    Mar. 3, 2022

Related U.S. Application Data

(60) Provisional application No. 62/832,933, filed on Apr. 12, 2019, provisional application No. 62/769,617, filed on Nov. 20, 2018.

(51) Int. Cl.
*G01N 27/22*    (2006.01)
*G01N 27/02*    (2006.01)
(Continued)

(52) U.S. Cl.
CPC ......... *G01N 27/026* (2013.01); *G01N 27/028* (2013.01); *G01N 33/48707* (2013.01)

(58) Field of Classification Search
CPC ...... G01N 27/02; G01N 27/026; G01N 27/22; G01N 33/28; G01N 33/487; G01N 33/48707; G01N 33/49; G01R 27/08
See application file for complete search history.

(56) References Cited

U.S. PATENT DOCUMENTS 5,208,163 A    5/1993    Charlton et al.
5,320,808 A    6/1994    Holen
(Continued)

FOREIGN PATENT DOCUMENTS

| CN | 108780056 | 11/2018 |
|---|---|---|
| JP | 2009031102 | 2/2009 |

(Continued)

OTHER PUBLICATIONS

Supplementary European Search Report in App. No. EP 19 88 6300, dated Jul. 5, 2022, 7 pages.
(Continued)

*Primary Examiner* — Neel D Shah
(74) *Attorney, Agent, or Firm* — Rankin, Hill & Clark LLP

(57) ABSTRACT

A DS sensing apparatus includes a body and electrodes provided on the body. The body defines a test volume between a first surface and an opposing second surface spaced from the first surface a distance that allows a fluid to enter the test volume from a fluid inlet, which is communicatively coupled to the test volume, via capillary action. The electrodes include a first sensing electrode on the first surface and configured to receive an input RF signal, a second sensing electrode on the first surface spaced from the first sensing electrode and configured to deliver an output RF signal and a floating electrode on the second surface.

18 Claims, 24 Drawing Sheets

(51) Int. Cl.
  *G01N 33/487*  (2006.01)
  *G01R 27/08*  (2006.01)

(56) References Cited

U.S. PATENT DOCUMENTS

| | | | |
|---|---|---|---|
| 5,346,672 A | 9/1994 | Stapleton et al. | |
| 5,381,510 A | 1/1995 | Ford | |
| 5,399,486 A | 3/1995 | Cathey et al. | |
| 5,478,751 A | 12/1995 | Oosta et al. | |
| 5,627,041 A | 5/1997 | Shartle | |
| 5,781,024 A | 7/1998 | Blomberg | |
| 6,555,386 B1 | 4/2003 | Rees | |
| 6,905,882 B2 | 6/2005 | Buechler | |
| 7,378,280 B2 | 5/2008 | Quake et al. | |
| 7,776,608 B2 | 8/2010 | Purcell | |
| 7,981,055 B2 | 7/2011 | Freeman et al. | |
| 8,105,841 B2 | 1/2012 | Blais et al. | |
| 8,158,062 B2 | 4/2012 | Dykes et al. | |
| 8,231,845 B2 | 7/2012 | Wyzgol et al. | |
| 9,081,001 B2 | 7/2015 | Cook et al. | |
| 9,678,069 B2 | 6/2017 | Gunnerson et al. | |
| 9,877,673 B2 | 1/2018 | Currie et al. | |
| 2005/0178663 A1 | 8/2005 | Kobayashi | |
| 2006/0065361 A1 | 3/2006 | Stiene | |
| 2006/0203236 A1* | 9/2006 | Ji | B01L 3/508 |
| | | | 356/246 |
| 2008/0058847 A1 | 3/2008 | Abe | |
| 2008/0257754 A1 | 10/2008 | Pugia et al. | |
| 2012/0040468 A1 | 2/2012 | Khaled | |
| 2014/0038308 A1 | 2/2014 | Murakami | |
| 2014/0073990 A1 | 3/2014 | Holmes | |
| 2014/0263279 A1* | 9/2014 | Vandersleen | B01L 7/00 |
| | | | 219/494 |
| 2015/0316454 A1 | 11/2015 | Wimberger-Friedl et al. | |
| 2015/0317506 A1 | 11/2015 | Xie | |
| 2015/0346131 A1* | 12/2015 | Mohseni | G01N 27/221 |
| | | | 29/846 |
| 2015/0352549 A1 | 12/2015 | Kolb | |
| 2016/0069913 A1 | 3/2016 | Bakhru | |
| 2016/0278680 A1 | 9/2016 | Bauer | |
| 2018/0303386 A1 | 10/2018 | Hall | |
| 2018/0371518 A1 | 12/2018 | Tsujimaru | |
| 2019/0054466 A1 | 2/2019 | Blais et al. | |

FOREIGN PATENT DOCUMENTS

| | | |
|---|---|---|
| JP | 2009281907 | 12/2009 |
| JP | 2011508872 | 3/2011 |
| JP | 2018512882 | 5/2018 |
| WO | 2009076247 | 6/2009 |
| WO | 2016172724 | 10/2016 |
| WO | 2017124104 | 7/2017 |
| WO | 2018/030958 | 2/2018 |

OTHER PUBLICATIONS

International Search Report filed in PCT/US2019/061613 dated Mar. 10, 2020.

* cited by examiner

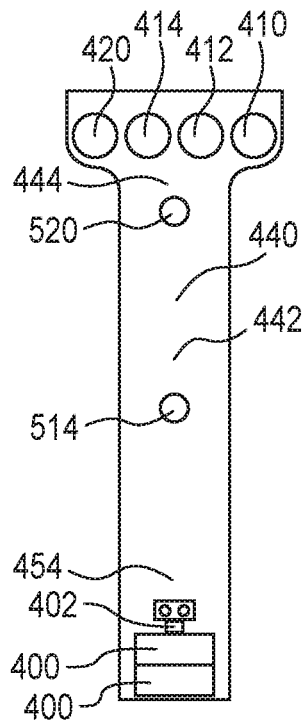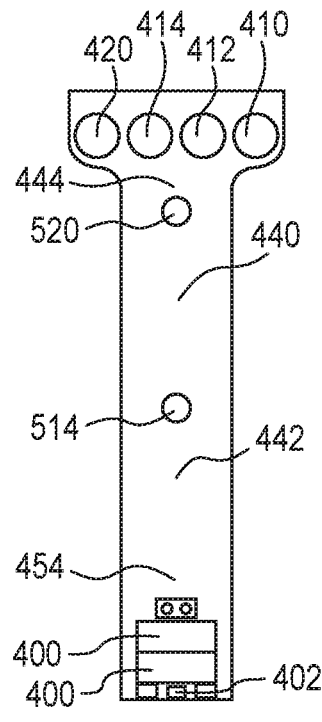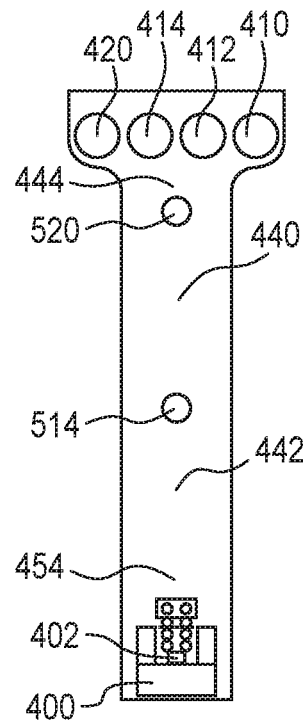
FIG. 14  FIG. 15  FIG. 16
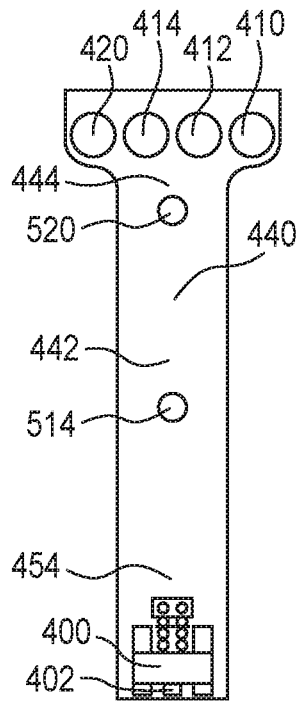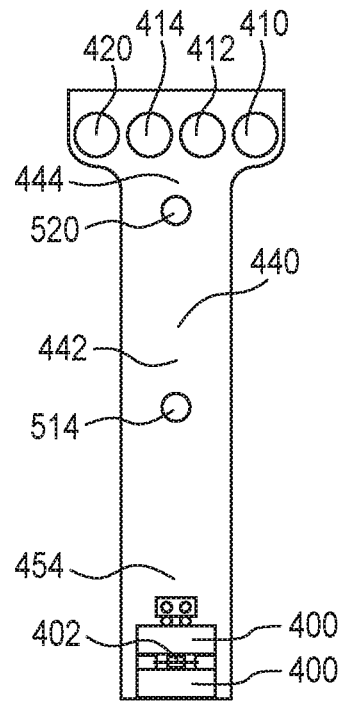
FIG. 17  FIG. 18

DIELECTRIC SPECTROSCOPY SENSING APPARATUS AND METHOD OF USE

BACKGROUND

Dielectric spectroscopy (DS) has been described as a useful analytical tool in the biomedical field as a label-free, non-destructive and real-time method to study the interaction of RF/microwave fields with biological/biochemical samples while requiring minimal sample preparation. Molecular characteristics of biomaterials such as human blood, spinal fluid, breast tissue and skin have been studied using DS for applications in disease detection and clinical diagnosis. Typical DS systems, however, tend to be large and expensive, making them cost-prohibitive in certain circumstances.

U.S. Pat. No. 9,995,701 B2 describes a DS system including a sensor having an input configured to receive an input radio frequency (RF) signal and an output to provide an output RF signal to an analyzer device. The sensor also includes substantially co-planar first and second sensing electrodes and a floating electrode. The first sensing electrode is coupled to the input and the second sensing electrode is coupled to the output. The floating electrode is spaced apart from the sensing electrodes by a space that defines a fluid channel that is communicatively coupled to receive a fluid material via a fluid port.

Improvements can be made in the aforementioned DS system to make the system more intuitive and user friendly.

SUMMARY

In view of the foregoing, a DS sensing apparatus includes a body defining a test volume between a first surface and an opposing second surface spaced from the first surface a distance that allows a fluid to enter the test volume from a fluid inlet, which is communicatively coupled to the test volume, via capillary action. The electrodes provided on the body include a first sensing electrode on the first surface and configured to receive an input radio frequency (RF) signal, a second sensing electrode on the first surface spaced from the first sensing electrode and configured to deliver an output RF signal and a floating electrode on the second surface.

BRIEF DESCRIPTION OF THE DRAWINGS

FIG. 14 is a flex circuit incorporated in the DS sensing apparatus according to another aspect of the present disclosure.

FIG. 15 is a flex circuit incorporated in the DS sensing apparatus according to another aspect of the present disclosure.

FIG. 16 is a flex circuit incorporated in the DS sensing apparatus according to another aspect of the present disclosure.

FIG. 17 is a flex circuit incorporated in the DS sensing apparatus according to another aspect of the present disclosure.

FIG. 18 is a flex circuit incorporated in the DS sensing apparatus according to another aspect of the present disclosure.

DETAILED DESCRIPTION

Figure 1:
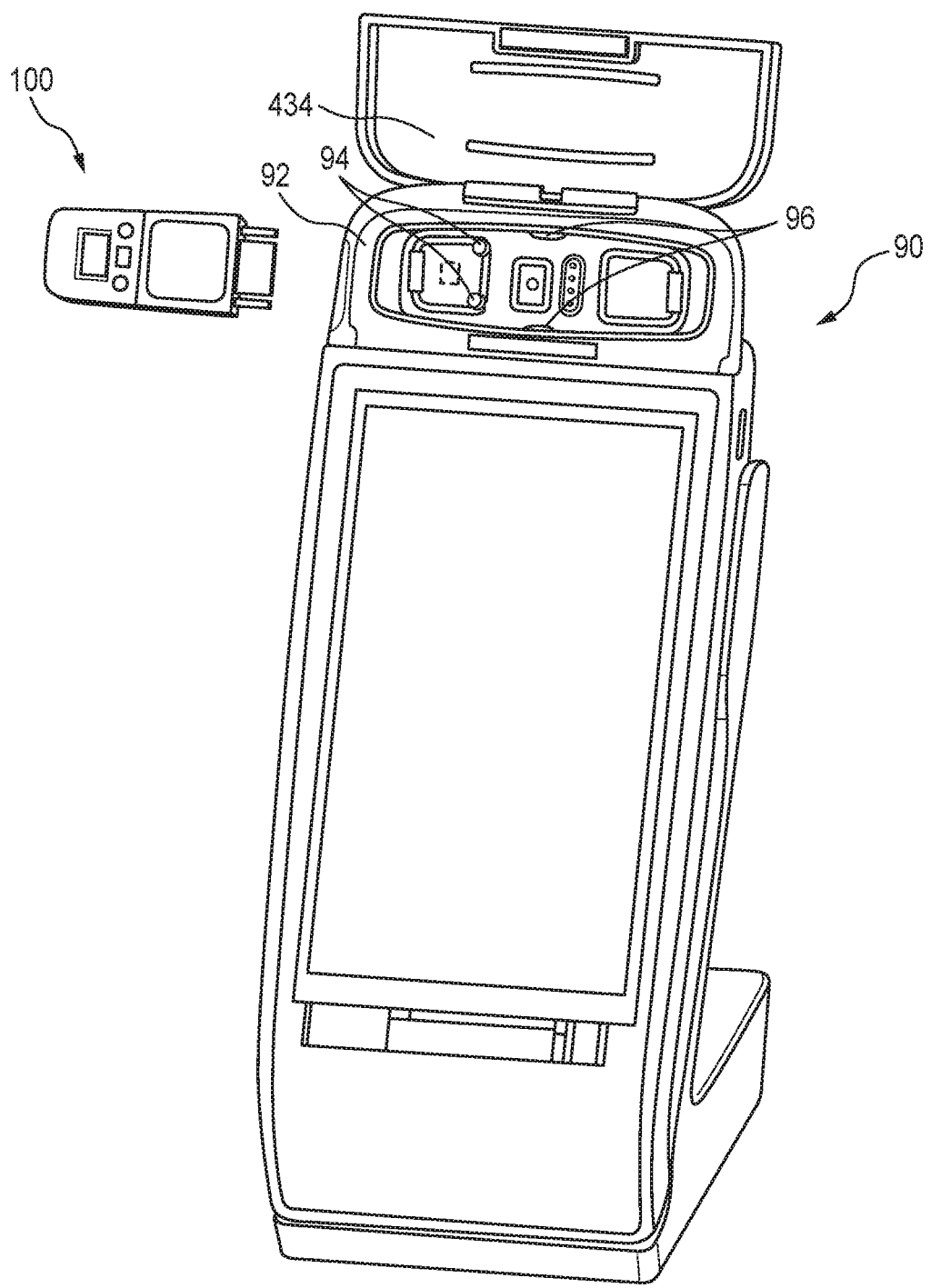
FIG. 1 is a perspective view of a DS sensing apparatus and an analyzer device.

It should, of course, be understood that the description and drawings herein are merely illustrative and that various modifications and changes can be made in the structures disclosed without departing from the present disclosure. Referring now to the drawings, wherein like numerals refer to like parts throughout the several views, FIG. 1 illustrates an analyzer device 90 including a housing 92 with pogo pins 94 and mating features 96 corresponding with a DS sensing apparatus 100. The analyzer device 90 is configured for receiving the DS sensing apparatus 100 in the housing 92, and connecting to the DS sensing apparatus 100 in a circuit via the pogo pins 94. FIGS. 2-8 illustrate the DS sensing apparatus 100 including a body 102 having a first body end portion 104 and a second body end portion 110. The DS sensing apparatus 100 includes a cap 112 that cooperates with the first body end portion 104 and the second body end portion 110. The body 102 is made from an upper body 114, a lower body 120, and a spacer 122 is interposed between the upper body 114 and the lower body 120 and connecting the upper body 114 with the lower body 120.

As depicted in FIGS. 2 and 4-6, the upper body 114 includes cut-outs 124 disposed between the first body end portion 104 and the second body end portion 110 that align with the mating features 96 of the analyzer device 90. In this manner, the cut-outs 124 and the mating features 96 are configured to ensure proper alignment between the DS sensing apparatus 100 and the analyzer device 90 when the DS sensing apparatus 100 is inserted into the analyzer device 90. Additionally, the cut-outs 124 each provide a gripping section for convenient handling by a user.

The spacer 122 is interposed between a first surface 130 defined by the lower body 120, and a second surface 132 defined by the upper body 114 and spaced from the first surface 130. The spacer 122 has a thickness that defines the spacing between the first surface 130 and the second surface 132. The spacer 122 thickness is 200-300 microns, and according to at least one embodiment, the spacer 122 thickness is 250 microns. The 250 micron spacer 122 may include a tolerance in thickness of 10 percent (i.e. ±25 microns). The spacer 122 includes a first spacer surface 134 that is planar and a second spacer surface 140 that is planar. When the DS sensing apparatus 100 is assembled, the first spacer surface 134 contacts the first surface 130, and the second spacer surface 140 contacts the second surface 132. According to at least one embodiment, the spacer 122 is a double-sided adhesive tape.

As depicted in FIGS. 5-8, a first assembly pin 142 and a first assembly hole 144 are provided on the first surface 130, disposed on the lower body 120 of the body 102. A first assembly aperture 150 defined by the spacer 122 is located to receive the first assembly pin 142 therethrough when the upper body 114 and the lower body 120 are assembled. A second assembly pin 152 and a second assembly hole 154 corresponding to the first assembly pin 142 and the first assembly hole 144 are provided on the second surface 132 and disposed on the upper body 114 of the body 102. A second assembly aperture 160 defined by the spacer 122 is located to receive the second assembly pin 152 therethrough when the upper body 114 and the lower body 120 are assembled. The assembly pins 142, 152 and assembly holes 144, 154 are configured respectively to snap together when the upper body 114 and the lower body 120 are assembled. Once the assembly pins 142, 152 and assembly holes 144, 154 are snapped together, a user cannot disassemble the lower body 120 and upper body 114 without damaging a portion of the DS sensing apparatus 100. In an embodiment, the upper body 114 and the lower body 120 are respectively fixed to the spacer 122 using at least one solvent weld. In an alternative embodiment, the upper body 114 and lower body 120 are fixed directly to each other using at least one solvent weld. One having ordinary skill in the art would appreciate that the same locking relationship between the assembly pins 142, 152 and corresponding assembly holes 144, 154 could be achieved by switching, or otherwise relocating the assembly pins 142, 152 and corresponding assembly holes 144, 154 about the first and second surfaces 130, 132.

As depicted in FIGS. 2-5, a buckle 162 provided at the first body end portion 104 of the lower body 120 includes a first lower finger 164, a second lower finger 170, and a lower support 172. The buckle 162 further includes a first upper finger 174, a second upper finger 180, and an upper support 182 extending from the upper body 114. The first lower finger 164 and the second lower finger 170 are each spaced from, and provided on opposite sides of the lower support 172. The first lower finger 164 and the second lower finger 170 are configured to deflect towards the lower support 172 when pushed toward the lower support 172. The first upper finger 174 and the second upper finger 180 are each spaced from, and provided on opposite sides of the upper support 182. The first upper finger 174 and the second upper finger 180 are configured to deflect towards the upper support 182 when pushed toward the lower support 172.

A first protuberance 184, a second protuberance 190, a third protuberance 192, and a fourth protuberance 194 are disposed on the first lower finger 164, second lower finger 170, first upper finger 174 and second upper finger 180 respectively. The protuberances 184, 190 disposed on the first lower finger 164 and the second lower finger 170 extend in a direction opposite from the lower support 172, and the protuberances 184, 190 disposed on the first upper finger 174 and the second upper finger 180 extend in a direction opposite from the upper support 182.

The cap 112 includes a first cap side wall 200 that defines a first cap opening 202 and a second cap side wall 204 that defines a second cap opening 210. Each of the first cap opening 202 and the second cap opening 210 is configured to receive two of the first, second, third, and fourth protuberances 184, 190, 192, 194 when the cap 112 is connected with the first body end portion 104, thereby locking the cap 112 in a fixed position relative to the body 102. Notably, the cap 112 is reversible with respect to the first body end portion 104, such that each of the first cap opening 202 and second cap opening 210 are configured to receive either the first and third protuberances 184, 192 or second and fourth protuberances 190, 194. In this manner, the cap 112 may engage the first body end portion 104 in two orientations distinguished by a 180 degree rotation of the cap 112 with respect to the first body end portion 104. To remove the cap 112 from the fixed position with the first body end portion 104, the protuberances 184, 190, 192, 194 are pushed inwards, out of the receiving cap openings 202, 210, thereby unlocking the cap 112 from the fixed position. As the protuberances 184, 190, 192, 194 are pushed out of the cap openings 202, 210, the fingers 164, 170, 174, 180 deflect toward the supports 172, 182, and the fingers 164, 170, 174, 180 are configured to retract to an undeflected position further away from the supports 172, 182 when not pushed inwards. In this manner, once connected, the cap 112 and the first body end portion 104 are configured to be disassembled without damaging any portion of the DS sensing apparatus 100.

As depicted in FIGS. 2-8, the second body end portion 110 is provided on an opposite end of the body 102, in a direction opposite from the first body end portion 104. The second body end portion 110 includes a fluid inlet 212 defined by a cantilever portion including a first fin 214 and a second fin 220 extending from the body 102 as part of the second body end portion 110. More specifically, the cantilever portion extends from a pedestal surface 222 that is offset from a ledge surface 224. The first fin 214 is integrally formed from the upper body 114 and extends the second surface 132 defined by the upper body 114, and the second fin 220 is integrally formed from the lower body 120 and extends the first surface 130 defined by the lower body 120. Both the pedestal surface 222 and the ledge surface 224 reside in respective planes that are normal to the direction in which the fins 214, 220 extend from the pedestal surface 222.

The pedestal surface 222 and the fins 214, 220 define a neck down portion 230. More specifically, each of the first fin 214 and the second fin 220 respectively includes a first side edge 232, 234 and a second side edge 240, 242 disposed inwards of an outer edge 244 of the ledge surface 224. In this manner, as shown in FIG. 2, the first fin 214 and the second fin 220 define the fluid inlet 212 that has a thinner front view profile than the pedestal surface 222 and the ledge surface 224.

The first surface 130 and the second surface 132 are spaced from each other such that the fins 214, 220 define a test volume 250 which fluid enters via capillary action from the fluid inlet 212, which is communicatively coupled to the test volume 250. The test volume 250 is less than 18 µL, and in accordance with at least one embodiment of the DS sensing apparatus 100, the test volume is about 9 µL. The fluid inlet 212 and test volume 250 are configured such that fluid entering the fluid inlet 212 and the test volume 250 via capillary action is drawn without a wicking element. Instead, the capillary action driving fluid flow is facilitated by the spacing between the upper body 114 and the lower body 120.

Figure 2:
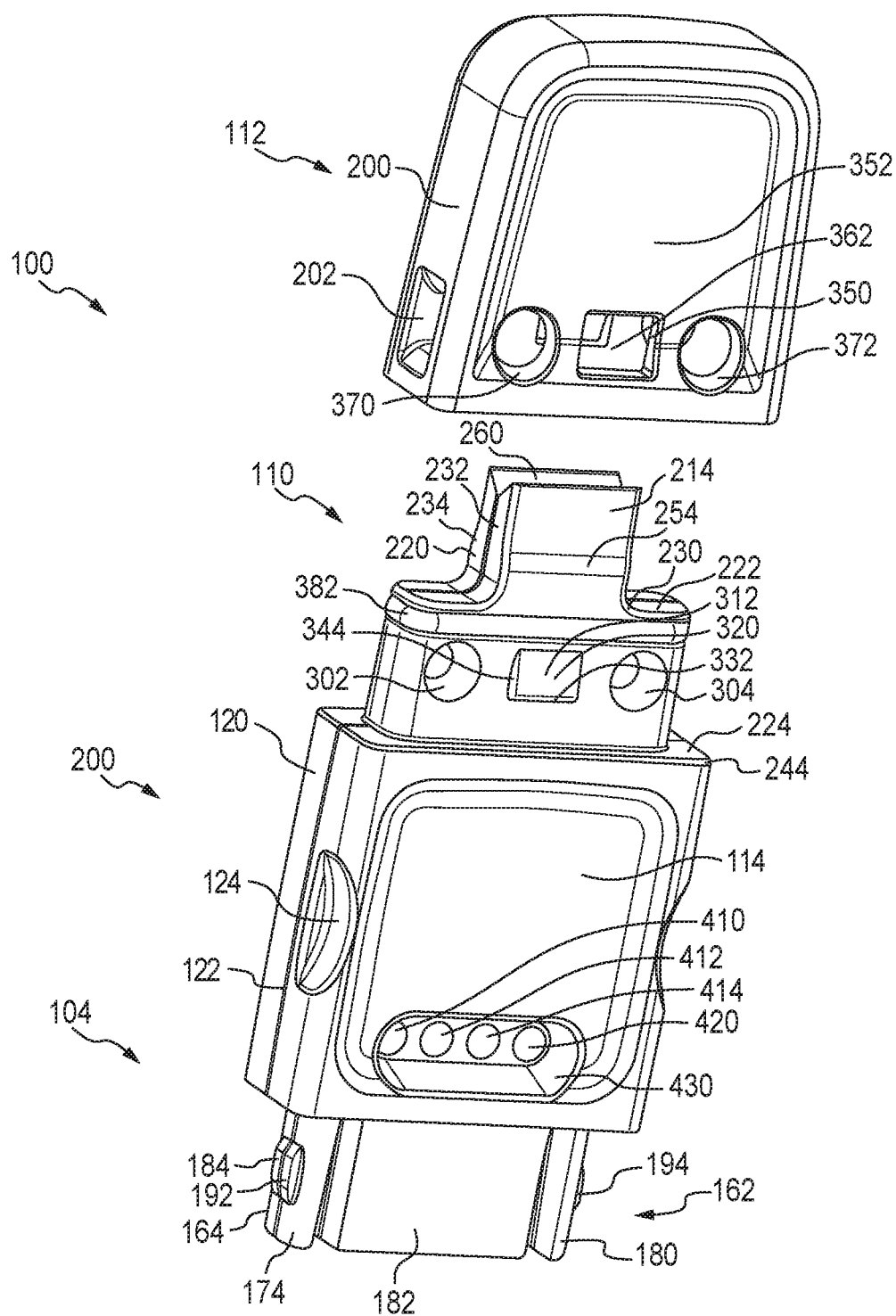
FIG. 2 is a perspective view of the DS sensing apparatus depicted in FIG. 1.
Figure 4:
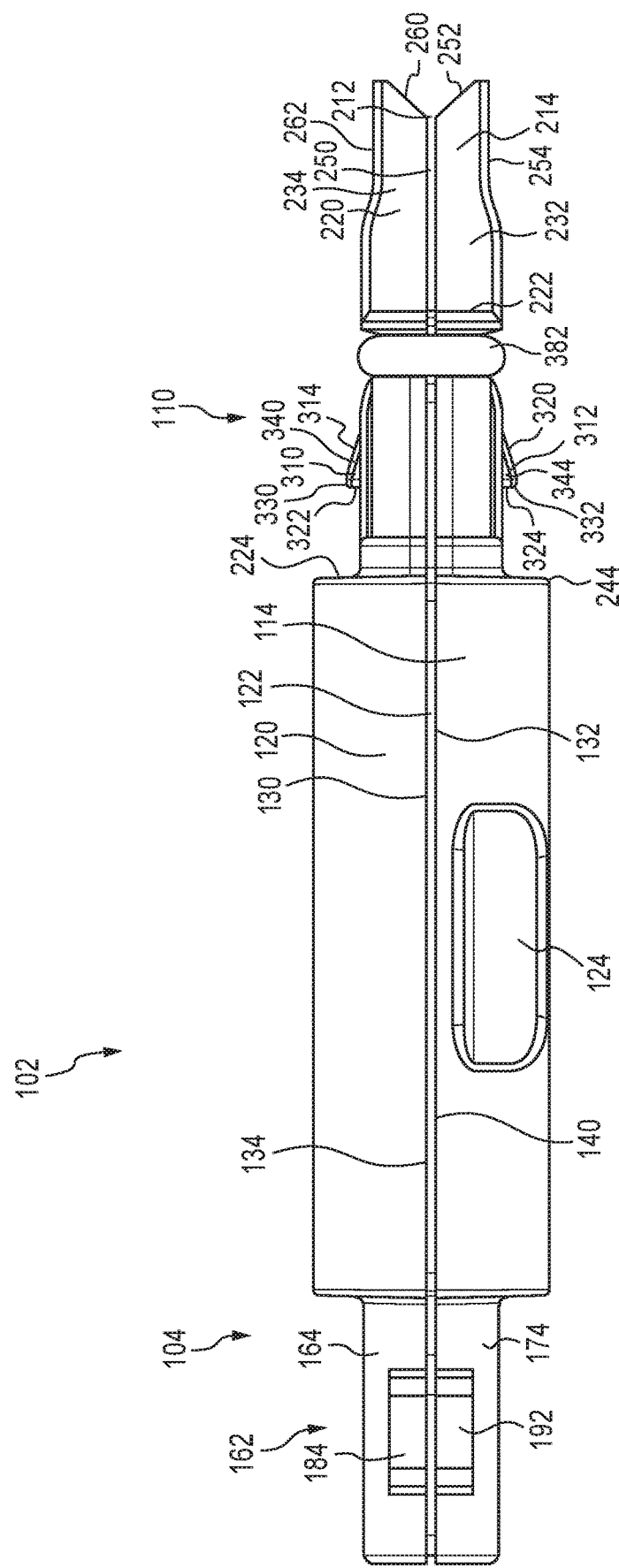
FIG. 4 is a side view of the DS sensing apparatus depicted in FIG. 1.
Figure 5:
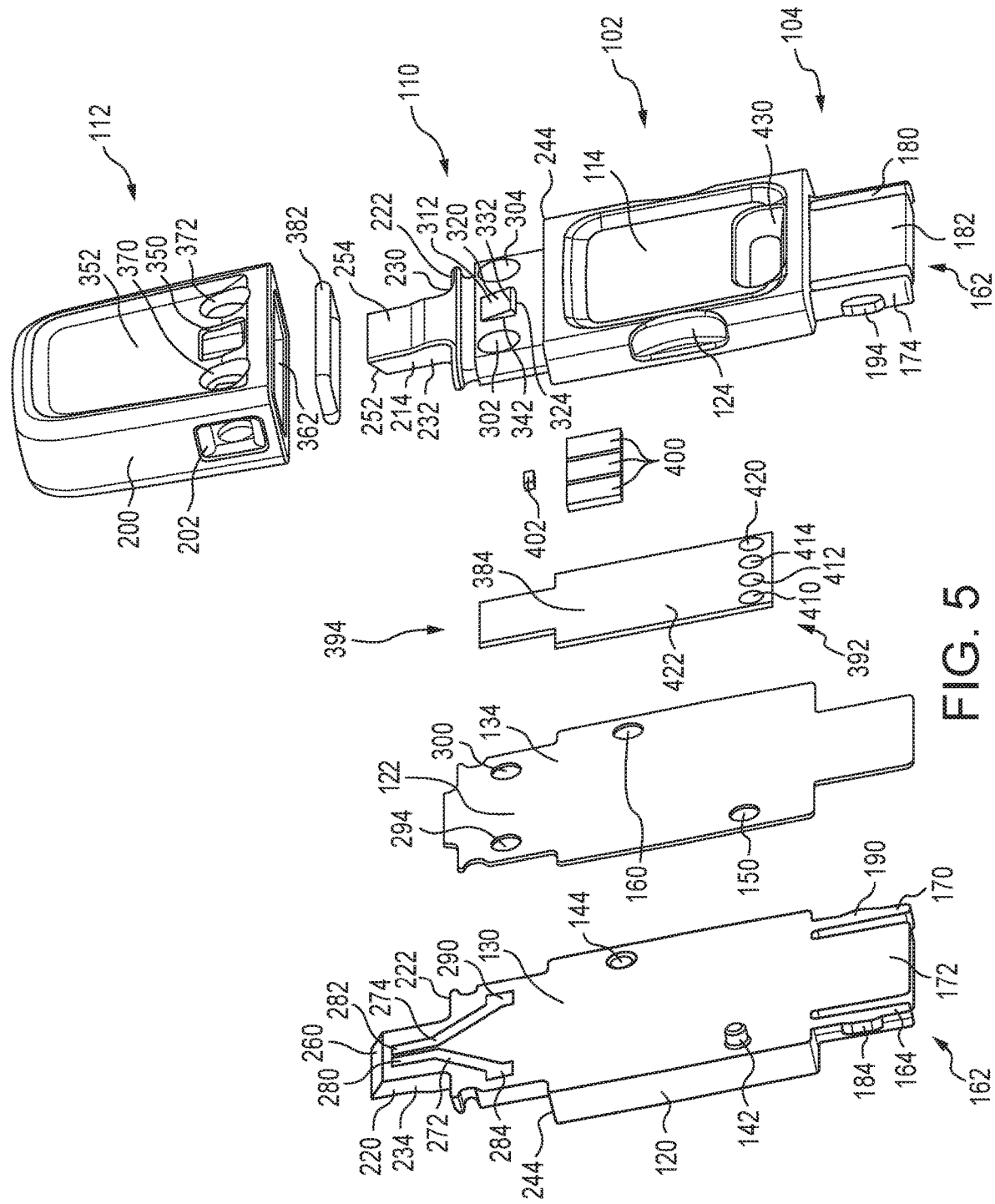
FIG. 5 is an exploded perspective view of the DS sensing apparatus depicted in FIG. 1.

As depicted in FIGS. 2, 4, and 5, the first fin 214 includes a first peripheral edge 252 that is angled from a first outer surface 254, toward the second surface 132 and the fluid inlet 212. The second fin 220 similarly includes a second peripheral edge 260 that is angled from a second outer surface 262 toward the first surface 130 and the fluid inlet 212.

Figure 3:
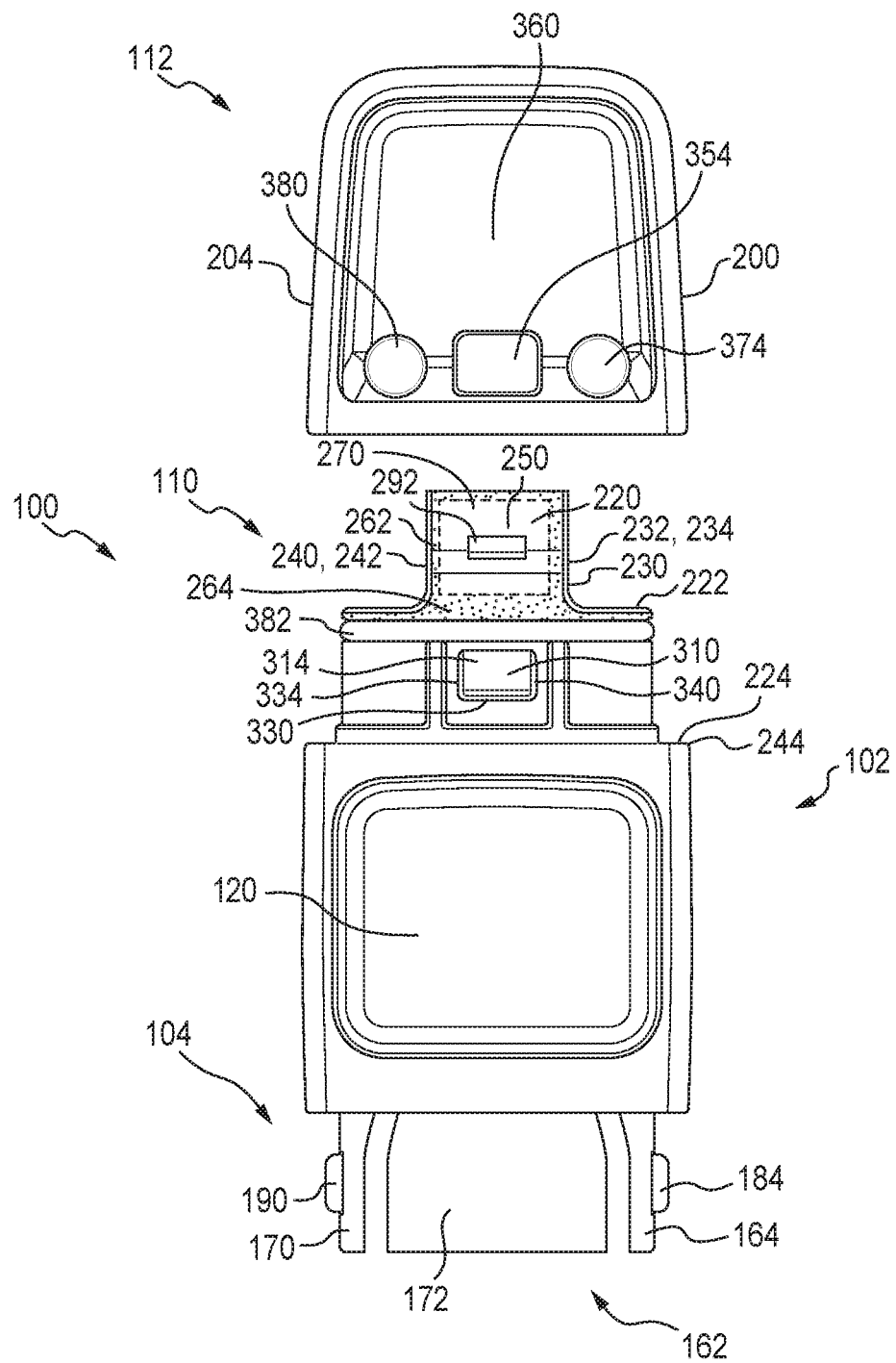
FIG. 3 is a plan view of the DS sensing apparatus depicted in FIG. 1.

The fluid inlet 212 in the illustrated embodiment is configured to receive fluid along the peripheral edges 252, 260 of the fins 214, 220. With reference to FIG. 4, the peripheral edges 252, 260 form a "less than" symbol ("<") shape taken from a side view of the body 102. This configuration allows a user of the DS sensing apparatus 100 to prick his/her skin, for example at one's finger, to deposit a droplet of blood between the first peripheral edge 252 and the second peripheral edge 260, which will then be drawn into the test volume 250, which obviates the need for a pipette or dropper to load the test volume 250 with a fluid to be tested. As shown in FIG. 3, the test volume 250 is generally rectangular when taken from a front view. As shown in FIGS. 3 and 4, the peripheral edges 252, 260 and side edges 232, 234, 240, 242 of the fins 214, 220 provide a rectangular test volume 250 that is open to ambient air when the cap 112 is not placed on the body 102.

When the fins 214, 220 take configurations other than rectangular, the peripheral edges 252, 260 can also take configurations other than linear. Also, the profile of each peripheral edge 252, 260 can be one of (1) a chamfer, which is shown in FIGS. 2, 4, and 5, (2) a radius, or (3) a combination of a chamfer and a radius. Also, indicia 264 such as frosting (stippled region in FIG. 3) on the fins 214, 220 can provide opaque or translucent sections that outline the test volume 250 and provide a location for a user to target a blood droplet. For example, as shown in FIG. 3, the test volume 250 is outlined by a visibly clear section 270 configured to provide visual indication to a user when fluid resides in a test volume 250.

As shown in FIGS. 3 and 5-8, electrodes, or at least portions thereof, reside in the test volume 250 to allow DS testing to be undertaken on the fluid within the test volume 250. After the fluid is loaded into the test volume 250 and the cap 112 is closed, the DS sensing apparatus 100 is configured to be inserted into the analyzer device 90 so that DS testing can be performed on the fluid within the test volume 250.

A first sensing electrode 272 and a second sensing electrode 274 are provided on the first surface 130 of the lower body 120 and extend from a respective first terminal end 280, 282 located on the first surface 130 within the test volume 250 to a respective second terminal end 284, 290 that is located on an opposite side of the pedestal surface 222. An adhesive is deposited between the spacer 122 and the first surface 130, and between the spacer 122 and the second surface 132 such that when fluid is provided in the test volume 250, the fluid is precluded from traveling between the spacer 122 and the first surface 130, and the spacer 122 and the second surface 132. With this construction, the sensing electrodes 272, 274 are deposited, e.g. printed onto the first surface 130 in such a manner that when covered by the spacer 122, which has adhesive deposited thereon, fluid in the test volume 250 is precluded from traveling beyond the pedestal surface 222 toward the second terminal ends 284, 290 of the respective sensing electrodes 272, 274. A floating electrode 292 is provided on the second surface 132 of the upper body 114 and is spaced from the sensing electrodes 272, 274 across the test volume 250. Each of the sensing electrodes 272, 274 and the floating electrode 292 can be an electrically conductive material (e.g., gold, copper or aluminum) deposited on the appropriate surface by, for example, sputter deposition using a shadow mask and lift-off process. In such an embodiment, each of the sensing electrodes 272, 274 and the floating electrode 292 can be formed with a thickness of 25 microns or less.

Figure 6:
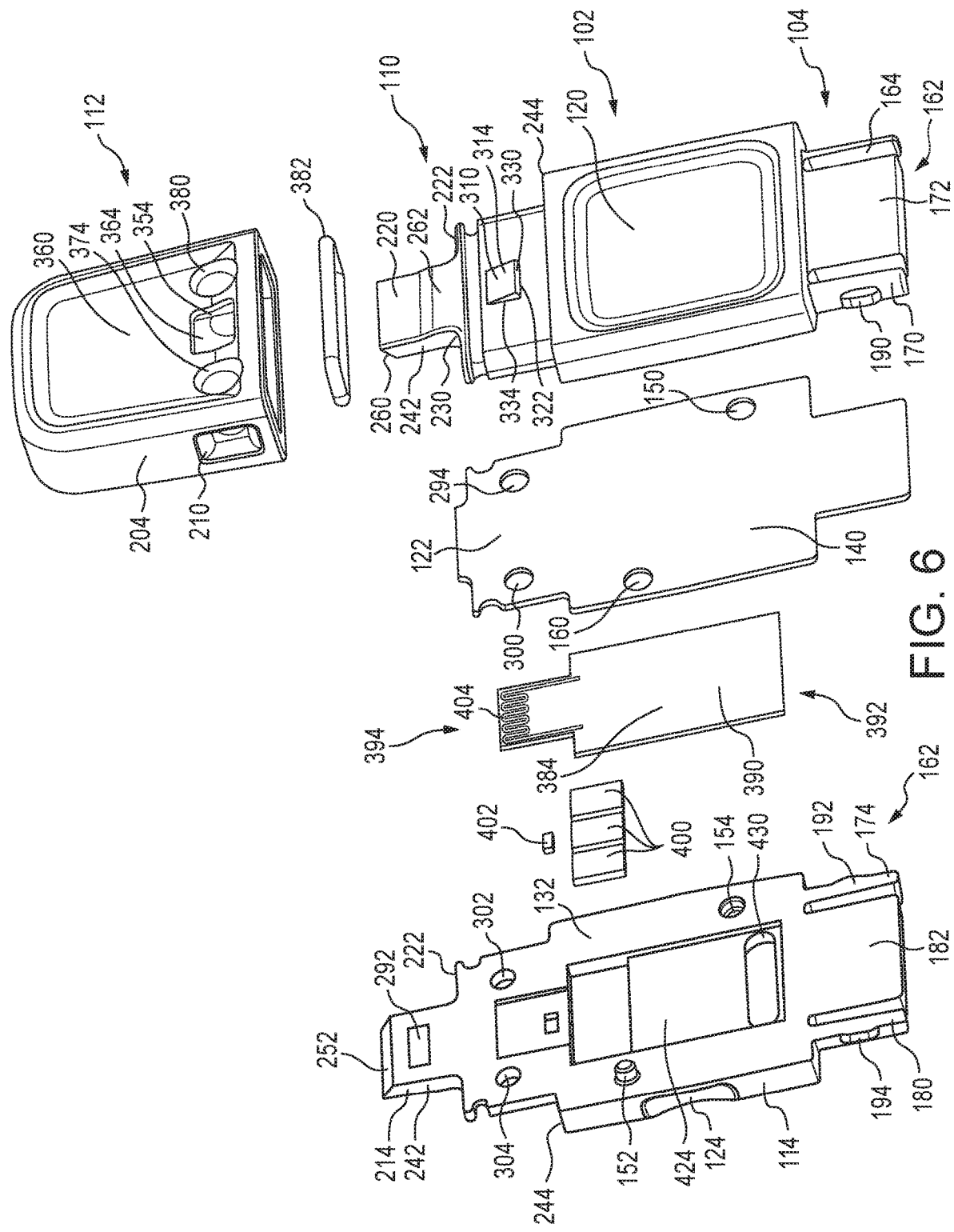
FIG. 6 is another exploded perspective view of the DS sensing apparatus depicted in FIG. 1.

As shown in FIGS. 5 and 6, the spacer 122 includes pin apertures 294, 300 that correspond with the second terminal ends 284, 290 of the sensing electrodes 272, 274 and pin openings 302, 304 of the upper body 114 when the spacer 122 is assembled with the upper body 114, exposing the second terminal ends 284, 290 to an exterior of the DS sensing apparatus 100 accessible to the analyzer device 90. As shown in FIGS. 2, 3, and 5, the second body end portion 110 of the upper body 114 defines the pin openings 302, 304 disposed between the pedestal surface 222 and the ledge surface 224. The pin openings 302, 304 align with the pin apertures 294, 300, respectively, in the spacer 122 when the spacer 122 is positioned on the upper body 114.

Connector or pogo pins 94 of the analyzer device 90 can extend through the pin openings 302, 304 and the pin apertures 294, 300 to provide for an electrical connection with the second terminal ends 284, 290 of the respective sensing electrodes 272, 274 and provide the appropriate input and output RF signals to the sensing electrodes 272, 274 which is described in more detail in U.S. Pat. No. 9,995,701 B2. Specifically, the first sensing electrode 272 on the first surface 130 is configured to receive an input RF frequency signal and the second sensing electrode 274 on the first surface 130, spaced from the first sensing electrode 272, is configured to deliver an output RF signal. When a sample is analyzed, the input RF signal bridges the test volume 250 through the sample, connecting the floating electrode 292 on the second surface 132 to the first sensing electrode 272 and the second sensing electrode 274 in a circuit.

As shown in FIGS. 2-6, the second body end portion 110 includes a first locking mechanism 310 integrally formed from the second outer surface 262 between the pedestal surface 222 and the ledge surface 224 of the lower body 120. The second body end portion 110 further includes a second locking mechanism 312 integrally formed from the first outer surface 254 between the pedestal surface 222 and the ledge surface 224, and further located between the pin openings 302, 304. According to one embodiment, the first locking mechanism 310 and the second locking mechanism 312 are integrally formed from the upper body 114 and the lower body 120, respectively.

Each of the first locking mechanism 310 and the second locking mechanism 312 are shaped as a wedge having a sloped face 314, 320 adjacent to the second body end portion 110, with each wedge shape pointing toward the test volume 250. The first and second locking mechanisms 310, 312 each respectively include a substantially vertical face 322, 324 adjacent to the respective sloped face 314, 320. The sloped faces 314, 320 and the substantially vertical faces 322, 324 respectively meet to form outward pointing edges 330, 332. The first and second locking mechanisms 310, 312 each respectively include two lateral faces 334, 340, 342, 344 disposed between the sloped faces 314, 320 and substantially vertical faces 322, 324. The sloped faces 314, 320, substantially vertical faces 322, 324, and lateral faces 334, 340, 342, 344 together respectively form the wedge shapes defining the first and second locking mechanisms 310, 312.

As shown in FIGS. 2, 3, 5, and 6, the cap 112 defines a first notch 350 within an upper cap wall 352 and a second notch 354 within a lower cap wall 360. As the cap 112 is connected with the second body end portion 110, inner surfaces 362, 364 of the upper cap wall 352 and lower cap wall 360 respectively slide over the sloped faces 314, 320 of the first locking mechanism 310 and the second locking mechanism 312. Each notch 350, 354 is capable of receiving either the first locking mechanism 310 or the second locking mechanism 312 when the cap 112 connects with the second body end portion 110. Once the locking mechanisms 310, 312 have engaged the notches 350, 354, the inner surfaces 362, 364 of the upper cap wall 352 and the lower cap wall 360 are unable to pass over the edges 330, 332 to disconnect the cap 112 from the second body end portion 110. In this manner, both the first locking mechanism 310 and the second locking mechanism 312 are configured to engage either the first notch 350 or the second notch 354 in a locked position. Once in the locked position with either the first notch 350 or the second notch 354, neither the first locking mechanism 310 nor the second locking mechanism 312 can be removed from the receiving notch 350, 354 without damaging a portion of the DS sensing apparatus 100. As a result, once the cap 112 is connected with the second body end portion 110, the cap 112 cannot be removed from the second body end portion 110 without damaging the DS sensing apparatus 100. One having ordinary skill in the art would appreciate that the same locking relationship between the cap 112 and the second body end portion 110 can be achieved by switching the locations of the first locking mechanism 310 and the second locking mechanism 312 with the locations of the first notch 350 and the second notch 354, respectively.

The cap 112 features pin holes 370, 372 defined within the upper cap wall 352, and pin holes 374, 380 defined within the lower cap wall 360. The pin holes 370, 372, 374, 380 are configured to receive the pogo pins 94 of the analyzer device 90, allowing the analyzer device 90 to access the pin openings 302, 304 when the cap 112 is assembled with the second body end portion 110. The pin holes 370, 372 on the upper cap wall 352 are coaxial with the pin holes 374, 380 on the lower cap wall 360. As a result, the cap 112 is reversible about the second body end portion 110, i.e. the cap 112 may engage the second body end portion 110 in two orientations distinguished by a 180 degree rotation of the cap 112 with respect to the second body end portion 110, and in each position the pin openings 302, 304 are accessible by the pogo pins 94.

As shown in FIGS. 2-6, the second body end portion 110 includes a gasket 382 disposed around the periphery of the second body end portion 110, located between the pin openings 302, 304 and the test volume 250. More specifically, the gasket 382 is located between the pin openings 302, 304 and the pedestal surface 222. When the cap 112 is assembled with the second body end portion 110, the cap 112 is disposed over the test volume 250, and the gasket 382 and the cap 112 form a liquid-tight seal such that fluid deposited at the fluid inlet 212 cannot pass over the gasket 382 toward the pin openings 302, 304. As a result, the liquid-tight seal prevents contamination of the pin openings 302, 304 by fluid in the test volume 250 when the cap 112 is connected with the second body end portion 110. Additionally, the cap 112 and the liquid-tight seal together are configured to close the second body end portion 110 from ambient air when the cap 112 is connected with the second body end portion 110, thereby preventing air from entering the test volume when the cap 112 is connected with the second body end portion 110. A liquid-tight seal can also be achieved, for example, by plastic-to-plastic contact between the cap 112 and the second body end portion 110.

As shown in FIGS. 2, 3, and 5-8 the DS sensing apparatus 100 may include a heating system configured for heating the test volume 250, including the sensing electrodes 272, 274 and test sample a (not shown), to a predetermined temperature. The heating system of the DS sensing apparatus 100 may be configured to heat the test volume 250 to 37° C.±0.5° C. within 30 seconds. In another embodiment, the test volume 250 may be heated to 37° C.±0.5° C. within 60 seconds. As shown in FIGS. 5-8, the DS sensing apparatus 100 heating system includes a support 384 that is a circuit support, which is a printed circuit board (PCB) in the depicted embodiment, provided between the upper body 114 and the lower body 120. More specifically, the support 384 is interposed between the upper body 114 and the spacer 122. A first support surface 390 is planar and contacts the first spacer surface 134. The support 384 is disposed within the body 102, including a first support end portion 392 disposed toward the first body end portion 104, and a second support end portion 394 extending in an opposite direction and toward the second body end portion 110. The second support end portion 394 extends into the second body end portion 110, terminating before reaching the gasket 382. In alternative embodiments similar to those illustrated in FIGS. 19-22, 28, and 29, the second support end portion 394 does not terminate prior to reaching the gasket 382, and extends further into the second body end portion 110.

Figure 7:
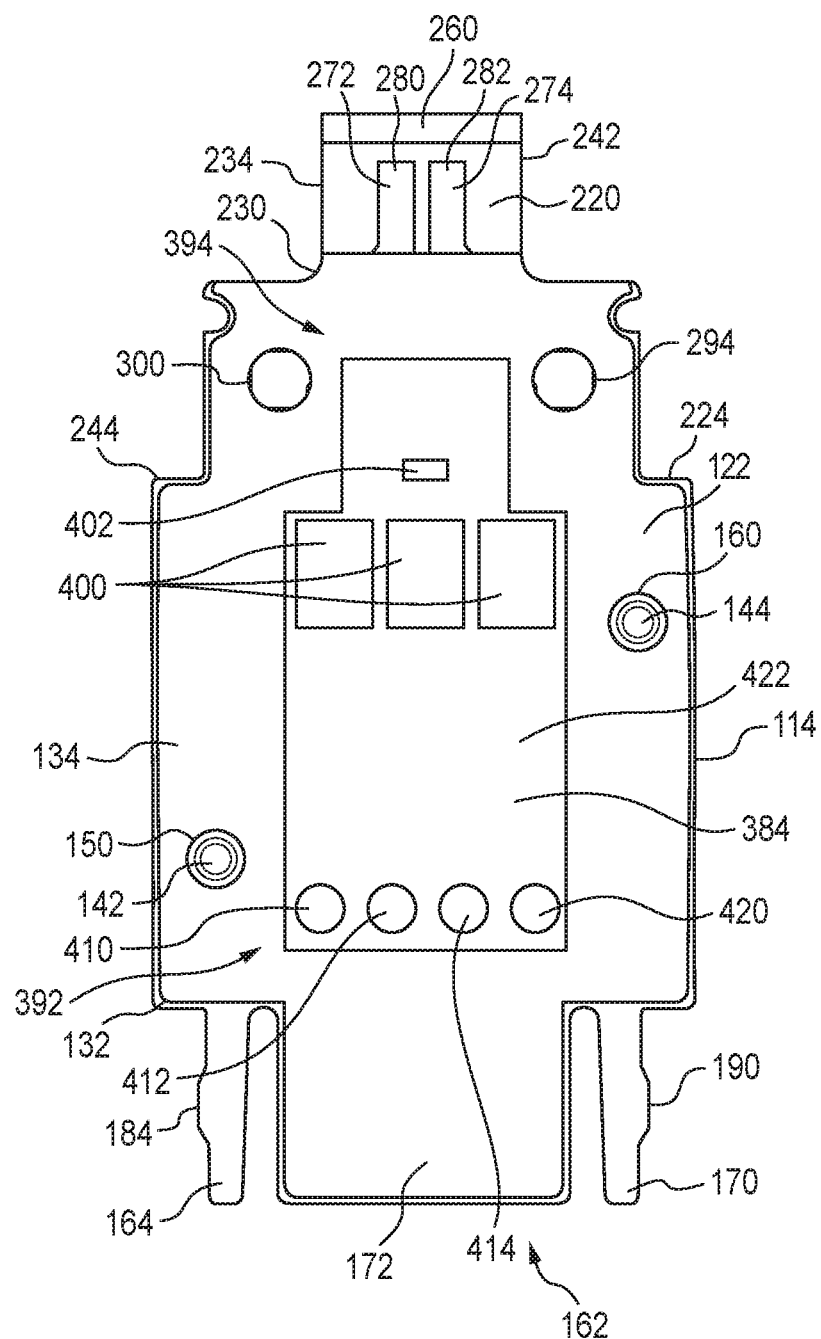
FIG. 7 is a disassembled plan view of the DS sensing apparatus depicted in FIG. 1.
Figure 8:
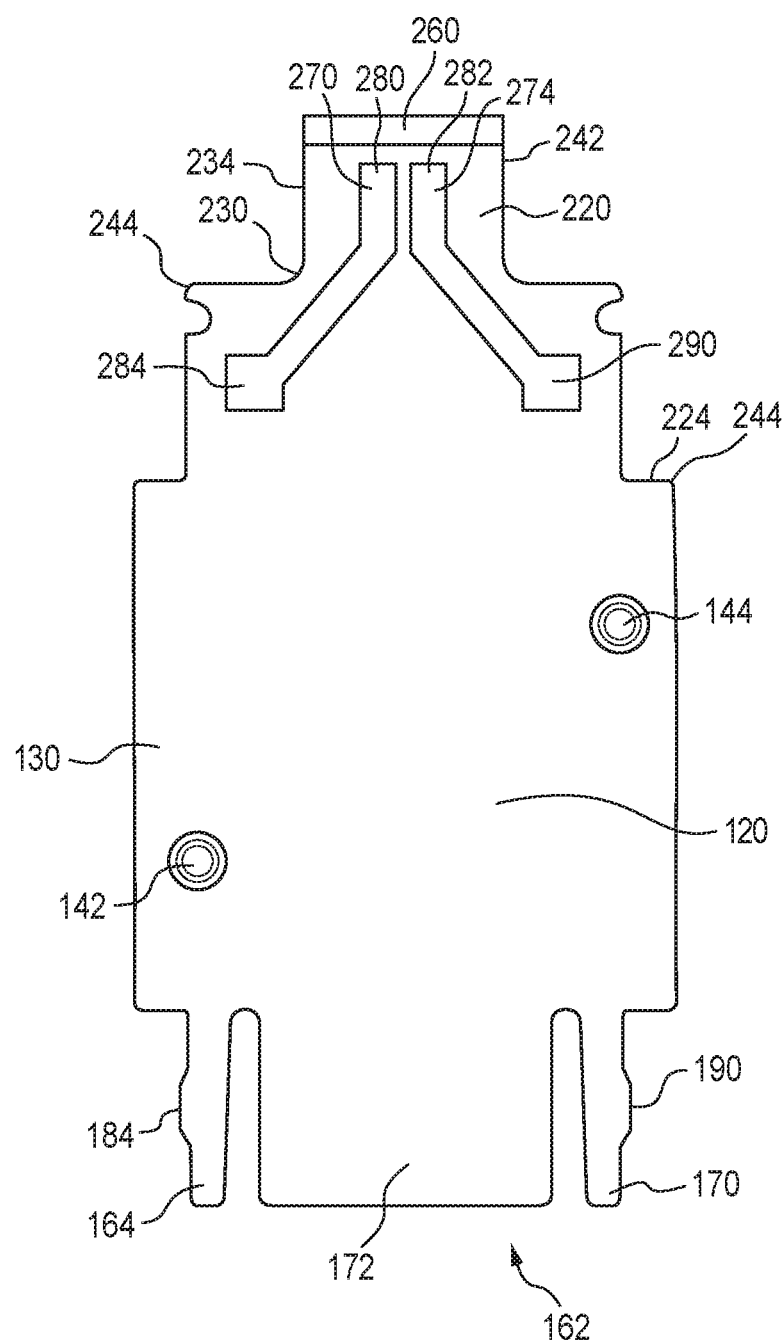
FIG. 8 is another disassembled plan view of the DS sensing apparatus depicted in FIG. 1.

Also shown in FIGS. 5-7, the heating system of the DS sensing apparatus 100 features at least one heater 400, a first thermistor 402, a conductive insert 404, and heating system circuitry connected with contacts 410, 412, 414, 420. Each of the first thermistor 402, the at least one heater 400, and the electrode contacts 410, 412, 414, 420 are disposed on a second support surface 422. The second support surface 422 is planar. The at least one heater 400 and the first thermistor 402 are disposed on the second support end portion 394. The at least one heater 400 is positioned on an opposite side of a liquid-tight seal as compared to the test volume 250 so as to preclude liquid from contacting the at least one heater 400.

With reference back to FIG. 6, the upper body 114 accommodates the heating system including the support 384, the at least one heater 400, and the first thermistor 402 in an upper body cavity 424. In this manner, while mounted on the support 384, the at least one heater 400 and the first thermistor 402 are spaced from the second surface 132 of the upper body 114. In an embodiment, the heating system components including the support 384, the at least one heater 400, and the first thermistor 402 are each spaced from the second surface 132 by about 5 millimeters in the upper body cavity 424. In an embodiment, the at least one heater 400 may perform cyclical thermal loading within a temperature range of 60° C. to 80° C. to bring the test volume 250 to a predetermined temperature. One having ordinary skill in the art would appreciate that placing the at least one heater 400 closer to the test volume 250 provides a greater level of control and efficiency in heating the test volume 250, and that this advantage can be further improved by insulating the at least one heater 400 and test volume 250 together from ambient temperature.

As shown in FIGS. 5-7, the heating system electrode contacts 410, 412, 414, 420 are disposed on the first support end portion 392. The contacts 410, 412, 414, 420 are laterally aligned in a row across the body 102. With respect to the body 102, the medial electrode contacts 412, 414 correspond to the first thermistor 402, and the lateral electrode contacts 410, 420 correspond to the at least one heater 400. The contacts are accessible to pogo pins 94 of the analyzer device 90 from the exterior of the DS sensing apparatus 100 through an upper body hole 430 defined by the upper body 114. One having ordinary skill in the art would appreciate that, while four electrode contacts are illustrated in FIGS. 5-7, electrodes and corresponding contacts may be added or rearranged as necessary to the support 384 in order to modify the heating system performance.

Figure 9:
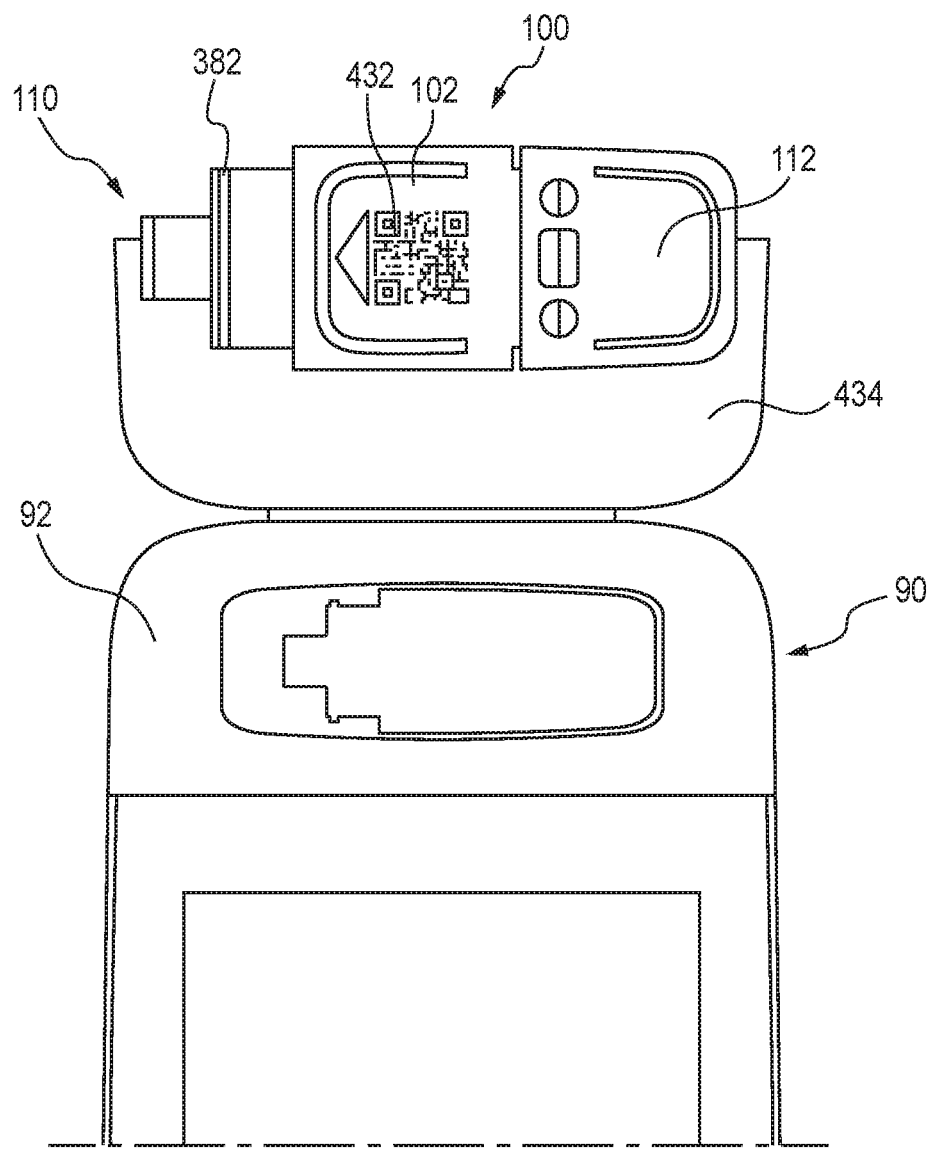
FIG. 9 is a plan view of the DS sensing apparatus and a analyzer device according to another aspect of the present disclosure.

FIG. 9 illustrates an embodiment of the DS sensing apparatus 100 featuring a barcode 432 disposed thereon. As shown, the barcode 432 is a QR code which may be used to identify a specific DS sensing apparatus 100. The housing 92 of the analyzer device 90 includes a door 434 for securing the DS sensing apparatus 100 in the analyzer device 90. The door 434 secures the DS sensing apparatus 100 in the housing 92 when the door 434 is closed over the DS sensing apparatus 100 in the housing 92. The analyzer device 90 is configured to scan the barcode 432 when the DS sensing apparatus 100 is placed in the housing 92.

Figure 10:
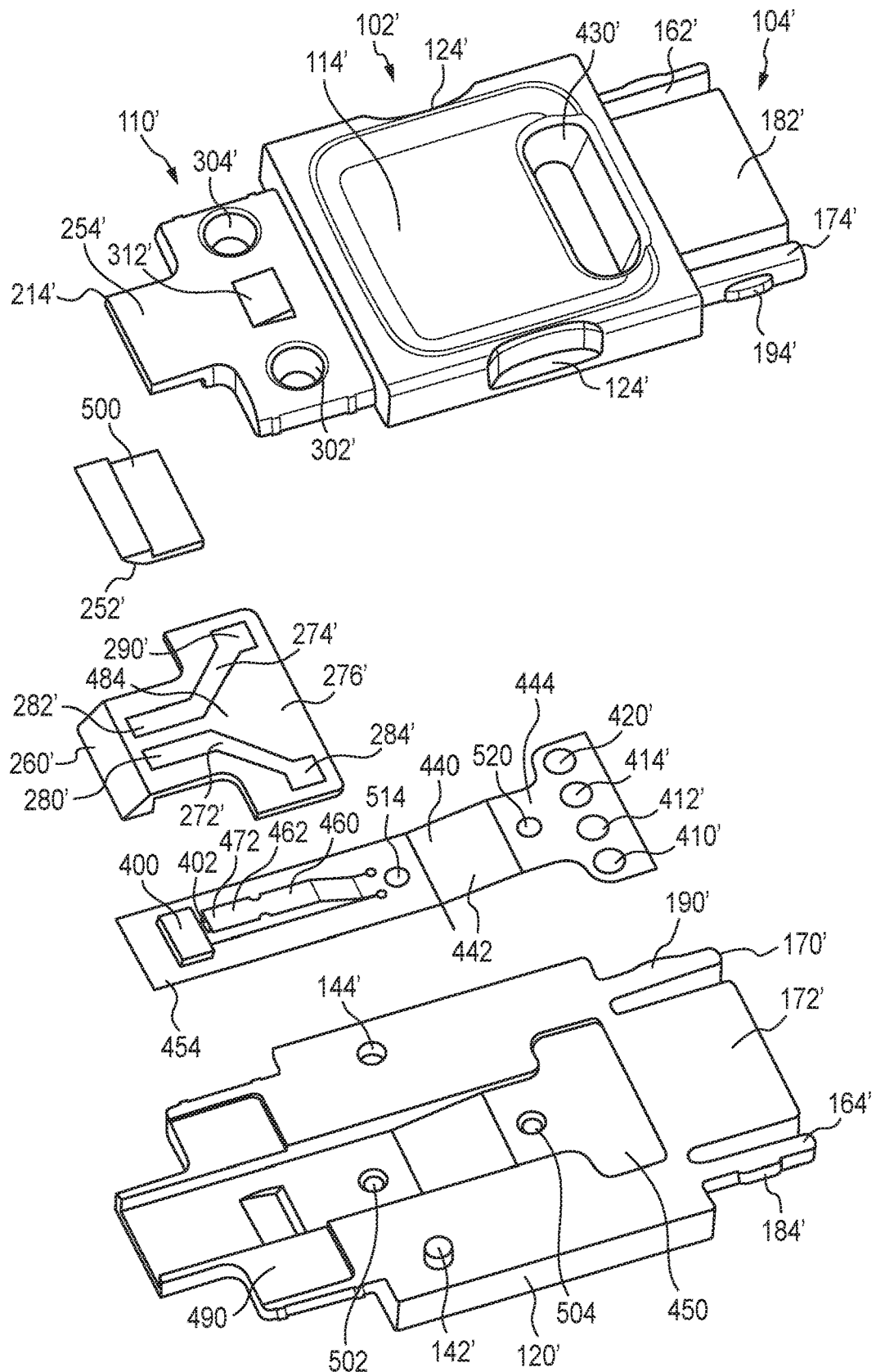
FIG. 10 is an exploded perspective view of a DS sensing apparatus according to another aspect of the present disclosure.

FIGS. 10-13 illustrate an alternate embodiment of the DS sensing apparatus 100 of FIGS. 1-8. In the embodiment of FIGS. 10-13, like elements with the DS sensing apparatus 100 of FIGS. 1-8 are denoted with the same reference numerals but followed by a primed suffix ('). FIG. 10 illustrates an embodiment of the DS sensing apparatus 100 including a flex circuit 440 featuring a support 442 that is a circuit support with the contacts 410', 412', 414', 420' disposed on the support 442, specifically a first support end portion 444. As shown, the support 442 is configured for insertion into the body 102' such that the support 442 is interposed between the upper body 114' and the lower body 120'. To this end, the lower body 120' features a lower body support cavity 450 defined in the first surface 130' configured for receiving the support 442, and the second surface 132' features a raised portion 452 corresponding to the lower body support cavity 450 that is configured to press the support 442 into the lower body support cavity 450 when the DS sensing apparatus 100 is assembled.

When the support 442 is assembled with the body 102', the first support end portion 444 is disposed toward the first body end portion 104', terminating before the lower support 172' and the upper support 182'. A second support end portion 454 of the support 442 extends in an opposite direction from the first support end portion 444 such that when the support 442 is assembled with the body 102' the second support end portion 454 is disposed toward the second body end portion 110'. A tab 460 integrally formed from the second support end portion 454 extends with a first tab surface 462 disposed along a downward sloping face 464 of the raised portion 452 and an offset face 470 of the upper body 114' that is offset from the raised portion 452. A distal end 472 of the tab 460 extends along the offset face 470 toward a first face 474 of a first injection molded step 480, ending on a side of the first injection molded step 480 opposite the test volume 250'. The first thermistor 402' is disposed at the distal end 472 of the tab 460, on a second tab surface 482 opposite the first tab surface 462. As shown, the second support end portion 454 extends through the second body end portion 110' to the fins 214', 220', between a first insert 484 and the lower body 120' such that the second support end portion 454 is separated from the fluid inlet 212' by the first insert 484 and housed in the lower body support cavity 450 at the second body end portion 110'.

Figure 11:
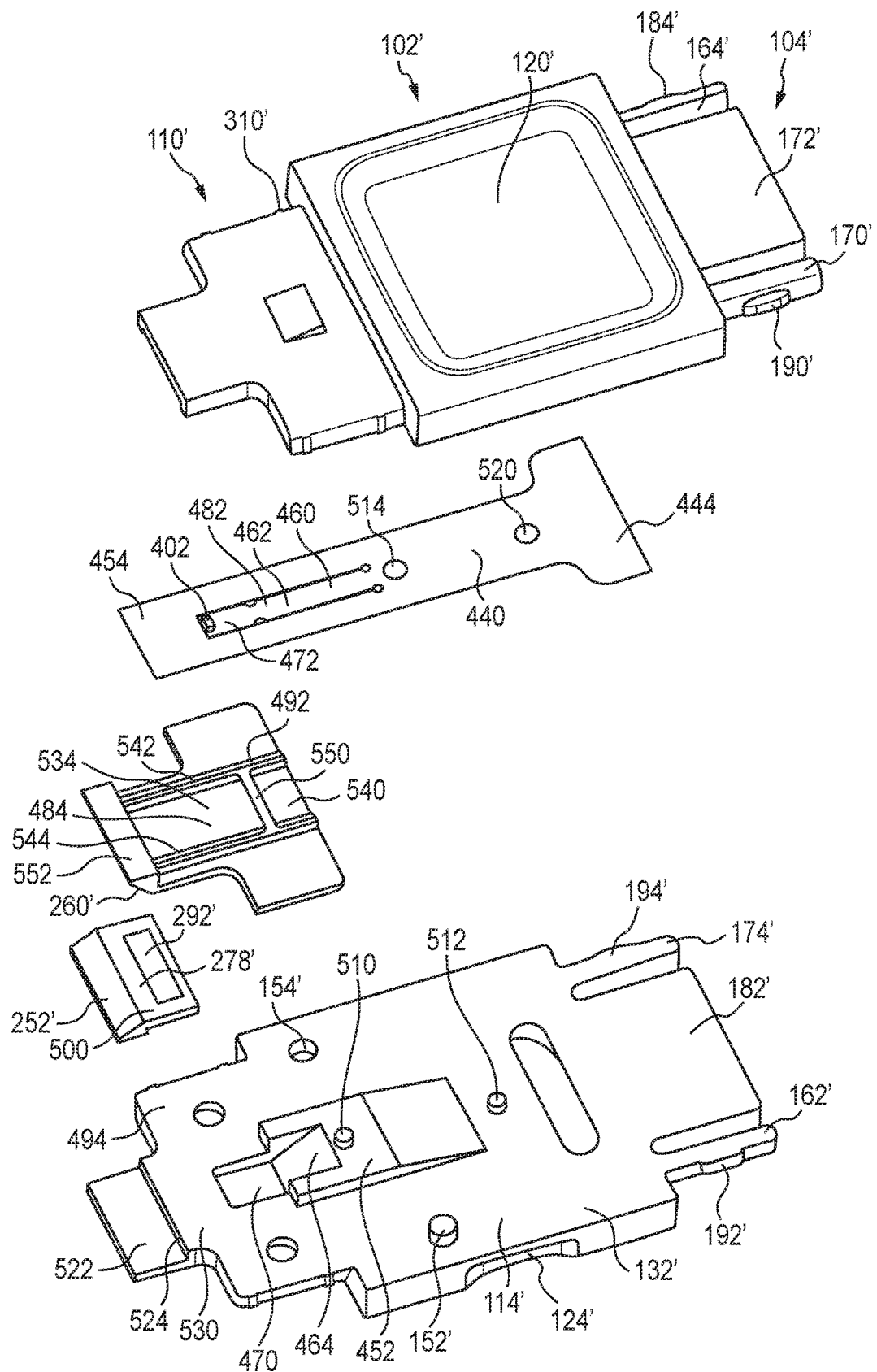
FIG. 11 is another exploded perspective view of the DS sensing apparatus of FIG. 10.
Figure 12:
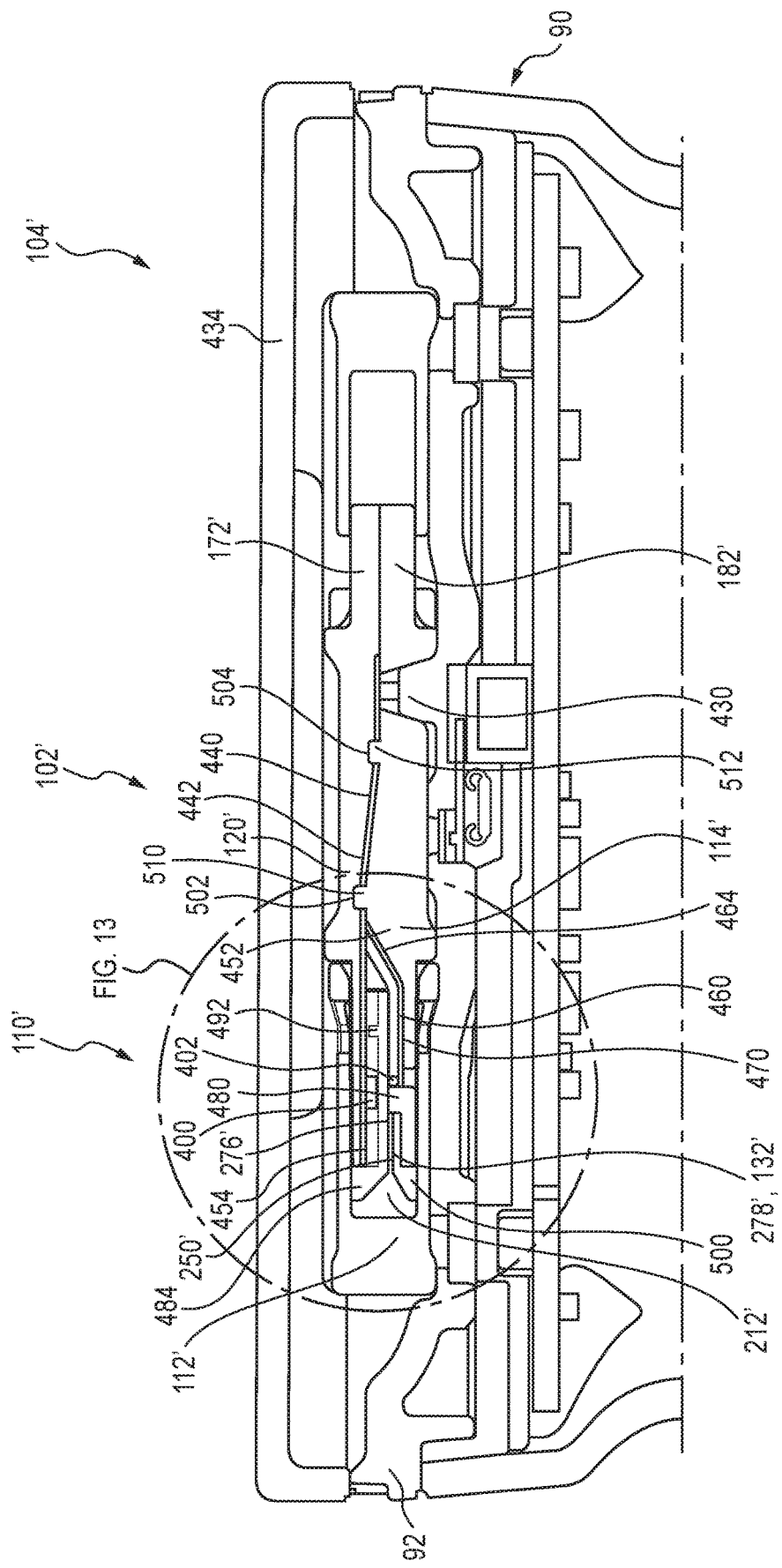
FIG. 12 is a cross-sectional side view of the DS sensing apparatus of FIG. 10.
Figure 13:
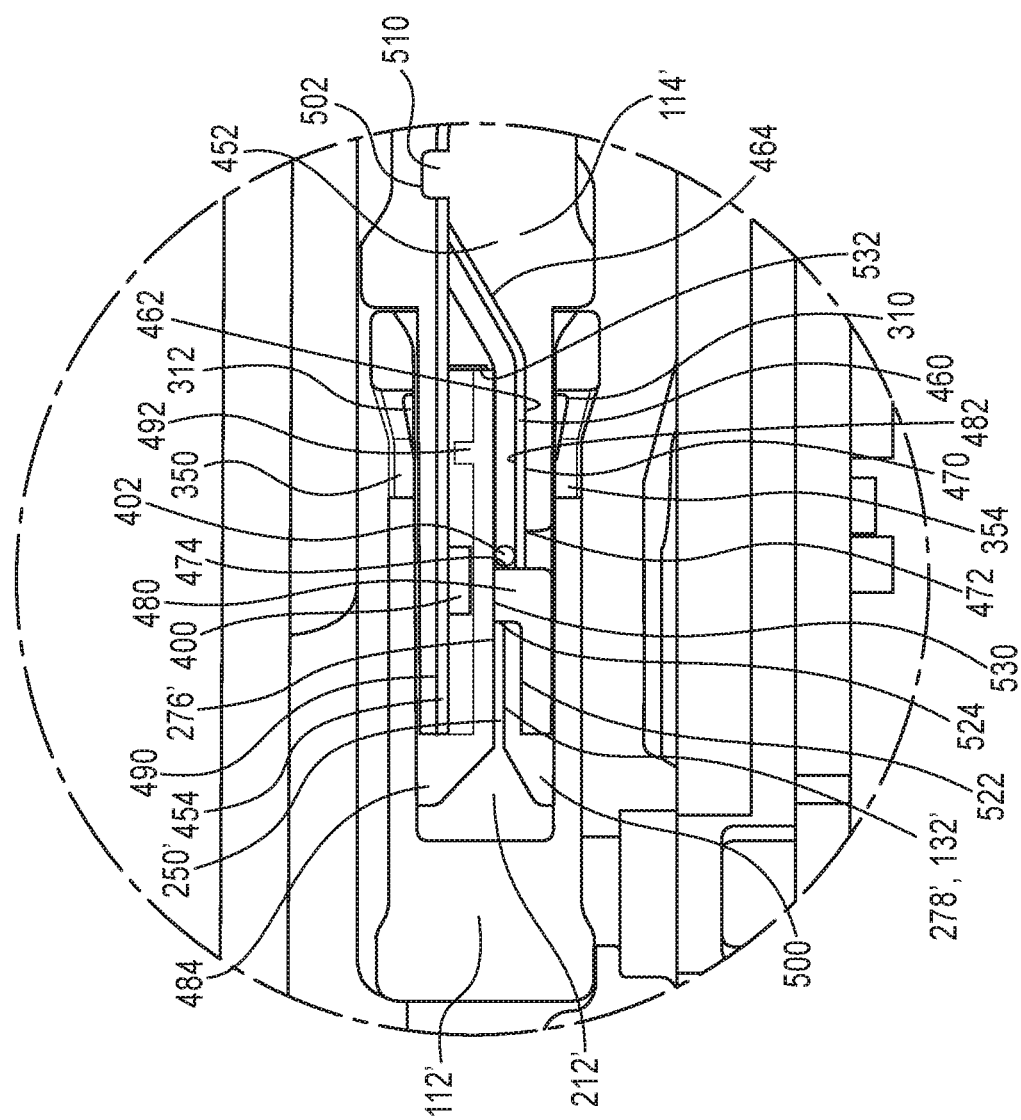
FIG. 13 is an enlarged partial view of the DS sensing apparatus of FIG. 12.
Figure 19:
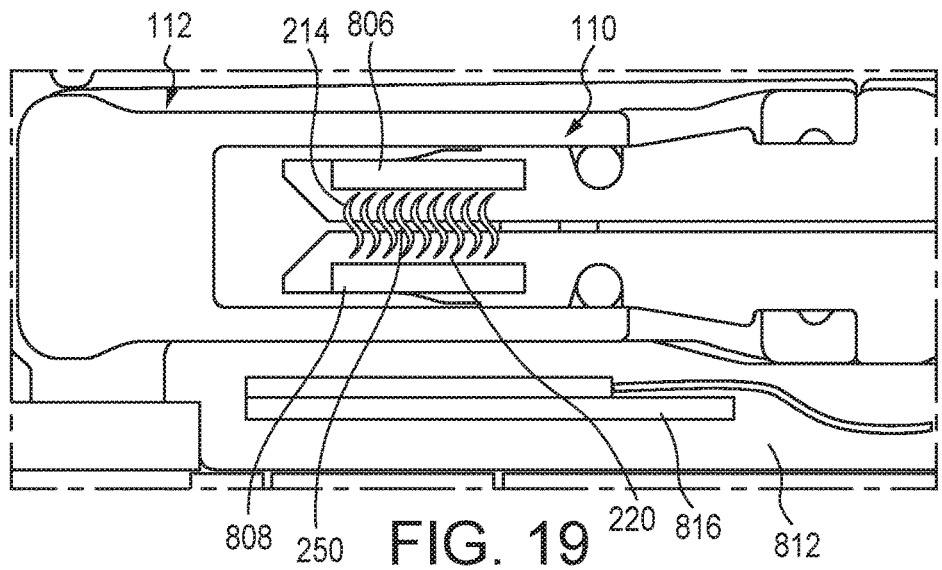
FIG. 19 is a partial, cross-sectional view of the DS sensing apparatus according to another aspect of the present disclosure.

As shown in FIG. 10, the first sensing electrode 272' and the second sensing electrode 274' are disposed on the first insert 484 which, as shown in FIGS. 12 and 13, forms at least a portion of the second fin 220' including the peripheral edge 260'. The first insert 484 is configured for assembly with the lower body 120' at the second body end portion 110', such that the first insert 484 is disposed over the first surface 130' defined by the lower body 120' at the second body end portion 110'. To this end, the lower body 120' features a lower body insert cavity 490 configured for receiving the first insert 484, and the first insert 484 includes at least one ridge 492 configured for engaging the flex circuit 440 in the lower body insert cavity 490. As shown in FIG. 11, the upper body 114' includes an upper body insert cavity 494 configured for receiving the first insert 484 such that the first insert 484 is disposed within the lower body insert cavity 490 and the upper body insert cavity 494 when the DS sensing apparatus 100 is assembled.

As shown in FIG. 11, the floating electrode 292' is disposed on a second insert 500, the second insert 500 being configured for assembly with the upper body 114' at the second body end portion 110'. As shown in FIGS. 12 and 13, when the second insert 500 is assembled with the upper body 114', the second insert 500 forms at least a portion of the first fin 214' including the peripheral edge 252', and the second surface 132' at the second body end portion 110' to define the test volume 250'. With this construction, the second peripheral edge 260' defined by the first insert 484 and the first peripheral edge 252' defined by the second insert 500 together form the fluid inlet 212', while an inner surface 276' of the first insert 484 and an inner surface 278' of the second insert 500 define the test volume 250'. The offset face 470 of the upper body 114' is offset from the raised portion 452 a distance that aligns the second tab surface 482 with the inner surface 276' of the first insert 484 to position the first thermistor 402' at a same elevation as the test volume 250' on a side of the injection molded step 480 opposite the test volume 250'.

In preparing the first insert 484 and the second insert 500 for assembly in the DS sensing apparatus 100, the first sensing electrode 272', the second sensing electrode 274' and the floating electrode 292' are disposed on a plurality of such inserts in a mass production fashion. As a result, depositing the first sensing electrode 272' and the second sensing electrode 274' on the first insert 484 and the floating electrode 292' on the second insert 500 improves the manufacturability of the DS sensing apparatus 100. As mentioned above, each of the sensing electrodes 272', 274' and the floating electrode 292' can be an electrically conductive material (e.g., gold, copper or aluminum) deposited on the appropriate surface by, for example, sputter deposition using a shadow mask and lift-off process. As opposed to having to mask the entire upper body 114 or lower body 120, for example in the embodiment depicted in FIGS. 2-8, in the embodiment depicted in in FIGS. 10-13, only the respective inserts 484, 500 need to be masked. As such, many more parts can be processed at the same manufacturing stage due to the relative small size of the inserts 484, 500 as compared to the upper body 114 or lower body 120. This can greatly reduce manufacturing costs.

As shown in FIG. 10, a third assembly hole 502 and a fourth assembly hole 504 are defined in the first surface 130' defined by the lower body 120'. The third assembly hole 502 and the fourth assembly hole 504 are laterally centered on the first surface 130', and as shown in FIG. 11, correspond with a third assembly pin 510 and a fourth assembly pin 512 which extend from the second surface 132' defined by the upper body 114' toward the lower body 120' when the DS sensing apparatus 100 is assembled. The third assembly pin 510 and the fourth assembly pin 512 are laterally centered on the second surface 132', and the flex circuit 440 defines a corresponding first flex circuit assembly aperture 514 and a second flex circuit assembly aperture 520. Notably, providing the DS sensing apparatus 100 with a plurality of flex circuit assembly apertures such as the first flex circuit assembly aperture 514 and the second flex circuit assembly aperture 520 prevents rotation of the flex circuit 440 relative to the upper body 114' and the lower body 120' when the DS sensing apparatus 100 is assembled.

The third assembly pin 510 and the fourth assembly pin 512 are respectively configured to snap with the third assembly hole 502 and the fourth assembly hole 504 when the upper body 114' and the lower body 120' are assembled. Once the third assembly pin 510 has formed a snap connection with the third assembly hole 502, and the fourth assembly pin 512 has formed a snap connection with the fourth assembly hole 504, a user cannot disassemble the lower body 120' and the upper body 114' without damaging a portion of the DS sensing apparatus 100. In an embodiment, the upper body 114' and the lower body 120' are respectively fixed to the support 442 and each other using at least one solvent weld. One having ordinary skill in the art would appreciate that the same locking relationships between the third assembly pin 510, the fourth assembly pin 512, the third assembly hole 502, and the fourth assembly hole 504 could be achieved by switching, or otherwise relocating the assembly pins 510, 512 and corresponding assembly holes 502, 504 about the first surface 130' and the second surface 132'.

As shown in FIGS. 12 and 13, when the DS sensing apparatus 100 is assembled the second insert 500 is seated on a first ledge surface 522 of the upper body 114' and abuts a second face 524 of the first injection molded step 480, the second face 524 of the first injection molded step 480 defining an opposite side of the first injection molded step 480 opposite from the first face 474 of the first injection molded step 480. A second ledge surface 530 is offset from the first ledge surface 522 by the first injection molded step 480, with the second ledge surface 530 formed as a part of the upper body insert cavity 494. With the first insert 484 disposed between the upper body 114' and the lower body 120' in the lower body insert cavity 490 and the upper body insert cavity 494, the first insert 484 is seated on the second ledge surface 530 and abuts a second injection molded step 532 formed from the raised portion 452 of the upper body 114'. The seated relationship of the first insert 484 and the second ledge surface 530 provides a seal therebetween that is impermeable to fluid from the test volume 250' such that a test sample in the test volume 250' is restricted from flowing between the first insert 484 and the second ledge surface 530 of the upper body 114'. A height of the second injection molded step 532 matches that of the first insert 484 from the second ledge surface 530 such that the first insert 484 is flush with the raised portion 452 of the upper body 114'. With this construction, a height of the test volume 250' is the offset distance between the first insert 484 and the second insert 500 defined by a height of the first injection molded step 480 over the second insert 500. The first insert 484, which is disposed in the upper body insert cavity 494, overlaps the flex circuit 440 disposed in the lower body support cavity 450 such that the flex circuit 440 is between the first insert 484 and the lower body 120' such that the second support end portion 454 is separated from the fluid inlet 212' by the first insert 484 and housed in the lower body support cavity 450 at the second body end portion 110'.

When the DS sensing apparatus 100 is assembled, the at least one ridge 492 spaces the first insert 484 from the flex circuit 440. In this manner, the first insert 484 and the flex circuit 440 are configured for accommodating the heater 400' on the second support end portion 454, on a side of the first insert 484 opposite the test volume 250', and the first thermistor 402' on the second tab surface 482 at the same elevation as the test volume 250', on a side of the first injection molded step 480 opposite the test volume 250'. Notably, positioning the first thermistor 402' at the same elevation as the test volume 250' is advantageous for tracking a temperature of the test volume 250'.

The first insert 484 includes at least one heating system cavity defined by the at least one ridge 492. As shown in FIG. 11, the first insert 484 includes a first heating system cavity 534 and a second heating system cavity 540 defined by the at least one ridge 492. The at least one ridge 492 includes a first side ridge 542 disposed on a side of the first insert 484 in a longitudinal direction of the first insert 484, a second side ridge 544 disposed on another side of the first insert 484 in the longitudinal direction of the first insert 484, and an intermediate ridge 550 disposed laterally across the first insert 484 between the first side ridge 542 and the second side ridge 544 so as to connect the first side ridge 542 and the second side ridge 544. The first heating system cavity 534 is further defined by a first insert projection 552 that connects the first side ridge 542 and the second side ridge 544.

Each of the first heating system cavity 534 and the second heating system cavity 540 is configured for receiving components of the heating system including the at least one heater 400' and the first thermistor 402'. The at least one heater 400' and the first thermistor 402' can be received in various combinations and positions within the first heating system cavity 534 and the second heating system cavity 540 relative to the test volume 250'. For example, the at least one heater 400' may be disposed in the first heating system cavity 534 with the first thermistor 402' disposed in the second heating system cavity 540. Alternatively, the first thermistor 402' may be disposed in the first heating system cavity 534 with the at least one heater 400' disposed in the second heating system cavity 540. With this construction, the at least one heater 400' is separated from the first thermistor 402' by the intermediate ridge 550. Also, the at least one heater 400' and the first thermistor 402' may be disposed together in the first heating system cavity 534 or the second heating system cavity 540.

As shown in FIG. 10, the flex circuit 440 includes the heater 400' and the first thermistor 402' disposed on the support 442. In the illustrated embodiment, the heater 400' is located in front of the first thermistor 402' with respect to the test volume 250'. A plurality of heaters 400' may be assembled with the first thermistor 402 in varying configurations. For example, FIG. 14 depicts an alternative embodiment of the flex circuit 440 featuring two heaters 400 with the first thermistor 402 located closer to the test volume 250' and farther from the first support end portion 444 than the first thermistor 402 with respect to the test volume 250'. FIG. 15 depicts an alternative embodiment of the flex circuit 440 featuring two heaters 400 located farther from the test volume 250' and closer to the first support end portion 444 than the first thermistor 402. FIG. 16 depicts an alternative embodiment of the flex circuit 440 featuring one heater 400 located closer to the test volume 250' and farther from the first support end portion 444 than the first thermistor 402 with respect to the test volume 250. FIG. 17 depicts an alternative embodiment of the flex circuit 440 featuring one heater 400 located farther from the test volume 250' and closer to the first support end portion 444 than the first thermistor 402. FIG. 18 depicts an alternative embodiment of the flex circuit 440 featuring two heaters 400 respectively disposed closer to and farther from the test volume 250' than the first thermistor 402.

In an embodiment, a second thermistor (not shown) is disposed within the DS sensing apparatus 100 and configured for measuring ambient temperature. The second thermistor is disposed within the DS sensing apparatus 100 such that the second thermistor is not accessible or visible from the exterior of the DS sensing apparatus 100. In an embodiment, ambient temperatures which the DS sensing apparatus 100 is designed to operate under range from 15° C. to 35° C.

Heating the test volume 250' may be accomplished with a variety of heater configurations. As another example, with reference to FIG. 19, an embodiment of the DS sensing apparatus 100 features end portion inserts including an upper insert 806 overmolded into the first fin 214, and a lower insert 808 overmolded into the second fin 220. Each of the upper insert 806 and the lower insert 808 may be made from steel, or another material appropriate for providing an induced current and generating heat. When the DS sensing apparatus 100 is inserted into an analyzer device 812, an induction coil 816 disposed within the analyzer device 812 and aligned with each insert 806, 808 is configured to induce a current in each insert 806, 808 that results in heating the test volume 250.

Figure 20:
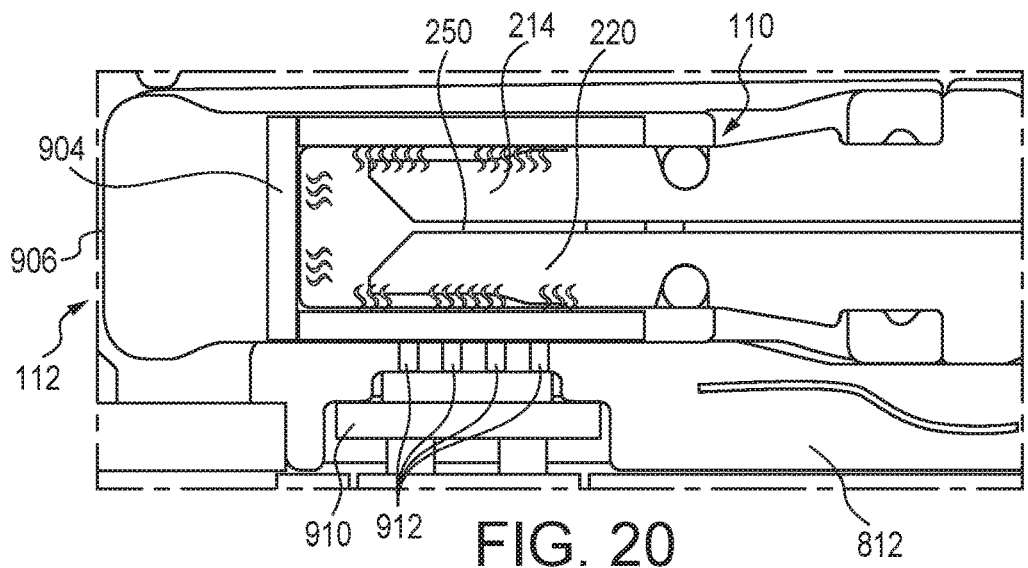
FIG. 20 is a partial, cross-sectional view of the DS sensing apparatus according to another aspect of the present disclosure.

FIG. 20 illustrates an embodiment of the DS sensing apparatus 100 featuring an overmolded cap insert 904 made of copper and disposed within the upper cap wall 352, lower cap wall 360, and a top 906 of the cap 112. When the cap 112 is connected with the second body end portion 110, the cap insert 904 faces the test volume 250 from at least three sides. An analyzer device heater 910 disposed within the analyzer device 812 is configured to generate thermal energy, and conduct thermal energy through thermal vias 912 to the cap insert 904 when the DS sensing apparatus 100 is inserted into the analyzer device 812. As thermal energy is conducted from the analyzer device heater 910 to the cap insert 904 disposed around the test volume 250, the cap insert 904 dissipates thermal energy within an interior of the cap 112 surrounding the test volume 250, thereby heating the test volume 250. In one method of use, the cap 112 may be preheated over a sufficient period of time to avoid any portion of the cap 112 exceeding a user contact temperature of 41° C.

Figure 21:
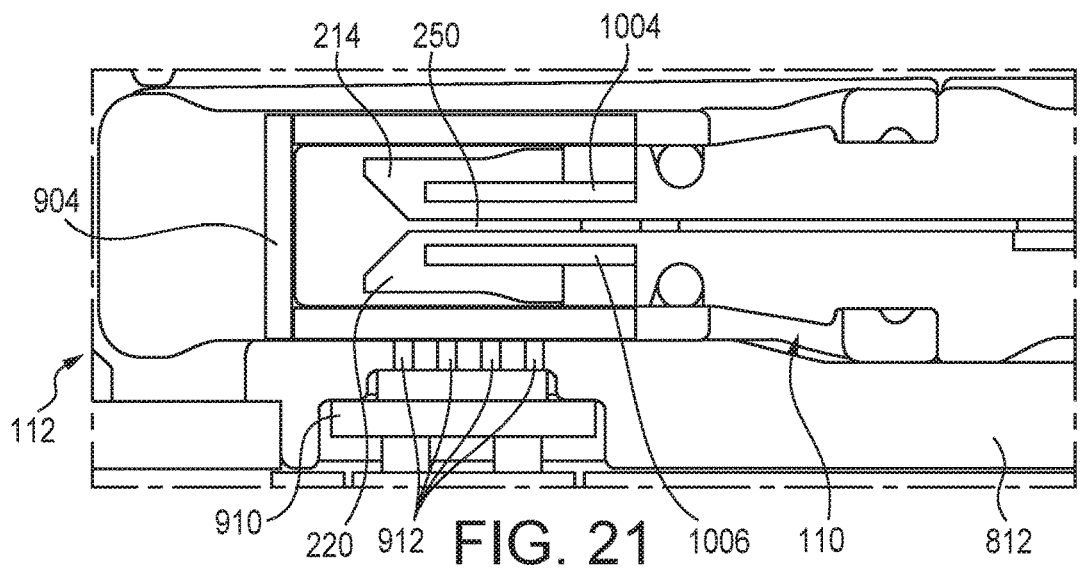
FIG. 21 is a partial, cross-sectional view of the DS sensing apparatus according to another aspect of the present disclosure.

FIG. 21 illustrates an embodiment of the DS sensing apparatus 100 featuring a modified upper insert 1004 and a modified lower insert 1006, each including a portion exposed to the exterior of the DS sensing apparatus 100. As depicted, each of the upper insert 1004 and the lower insert 1006 are made from copper, and are partially exposed to the exterior of the DS sensing apparatus 100. The exposed portions of the upper and lower inserts 1004, 1006 are configured to connect with the cap insert 904 when the cap 112 is connected with the second body end portion 110. As a result, when the analyzer device heater 910 conducts thermal energy to the cap insert 904, in addition to dissipating thermal energy within the interior of the cap 112, the cap insert 904 conducts thermal energy to the upper and lower inserts 1004, 1006. In this manner, thermal energy is conducted within the first fin 214 and second fin 220, more directly heating the test volume 250 relative to the embodiment illustrated in FIG. 20.

Figure 22:
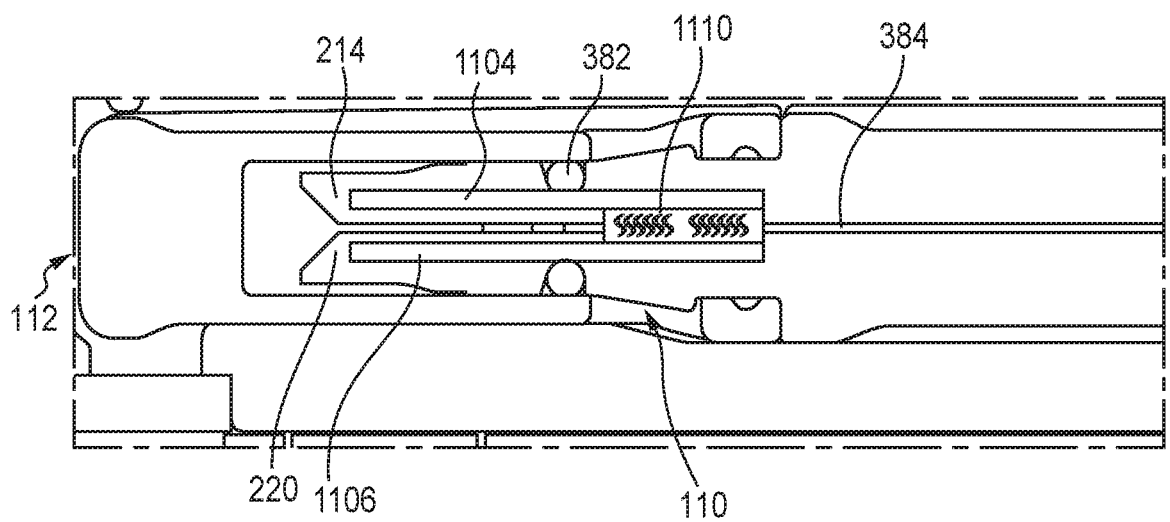
FIG. 22 is a partial, cross-sectional view of the DS sensing apparatus according to another aspect of the present disclosure.

FIG. 22 illustrates an embodiment of the DS sensing apparatus 100 featuring a modified upper insert 1104 disposed in the first fin 214, and a portion of the upper insert 1104 extends passed the gasket 382, terminating within the second body end portion 110. A modified lower insert 1106 is disposed in the second fin 220, and a portion of the lower insert 1106 extends passed the gasket 382, terminating within the second body end portion 110. Each of the upper insert 1104 and the lower insert 1106 is connected to a heater 1110 disposed in the support 384, and configured to conduct thermal energy from the heater 1110 to the test volume 250, thereby heating the test volume 250. The heater 1110 is powered by an energy storage unit (not shown) which may be a capacitor. As a capacitor, the energy storage unit may also be a supercapacitor. The energy storage unit is connected to the heater and charged from an external power source, such as the analyzer device 812. Further, contacts similar to contacts 410, 412, 414, 420, can be provided on the support 384 to receive power from the analyzer device 812 prior to a patient loading the test volume 250 with blood.

Figure 23:
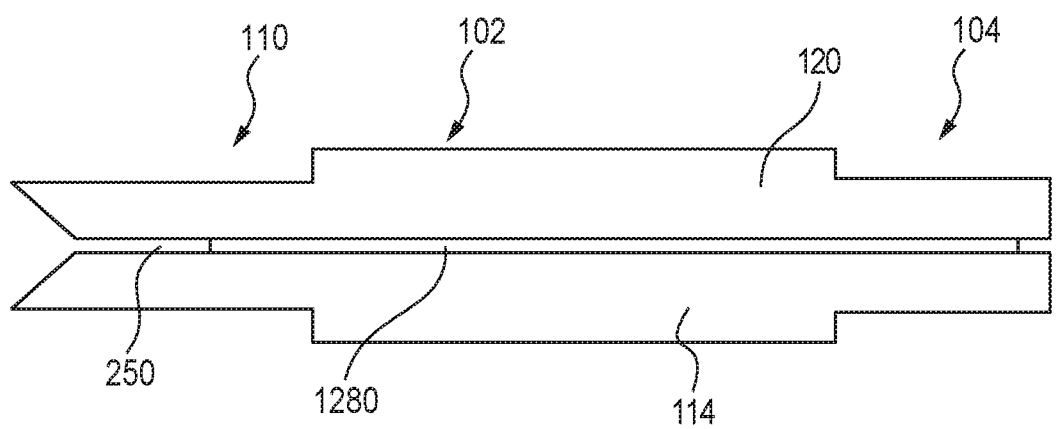
FIG. 23 is a schematic cross-sectional view of the body of the DS sensing apparatus according to another aspect of the present disclosure.
Figure 24:
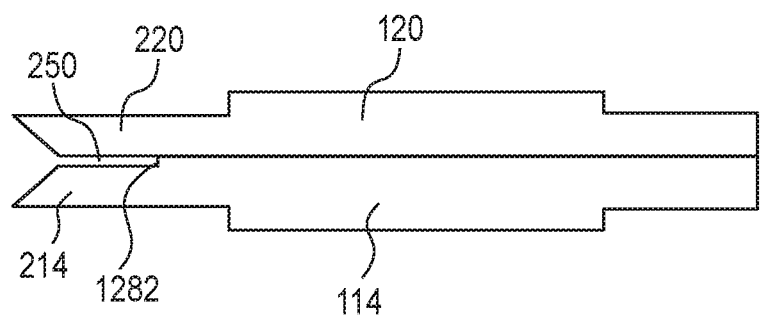
FIG. 24 is a schematic cross-sectional view of the body of the DS sensing apparatus according to another aspect of the present disclosure.

Independent from the heating system embodiments of the DS sensing apparatus 100, one having ordinary skill in the art would also appreciate that alternatives to the spacer 122 as double sided adhesive tape may be provided to otherwise space the upper body 114 and lower body 120. For example, FIG. 23 illustrates a modified spacer 1280 as a solid acrylic plate having a thickness of 250 microns, and fixed between the upper body 114 and the lower body 120. The modified spacer 1280 may include a tolerance of 10 percent (i.e. ±25 microns). In an alternative embodiment illustrated in FIG. 24, the DS sensing apparatus 100 features an injection molded step 1282 formed on the second surface 132 of the upper body 114, spacing a portion of the lower body 120 and upper body 114 according to the height of the injection molded step 1282. The injection molded step 1282 is 250 microns and may include a tolerance of 10 percent (i.e. ±25 microns). One having ordinary skill in the art would appreciate that the injection molded step 1282 may be formed either from the upper body 114 or lower body 120.

Figure 25:
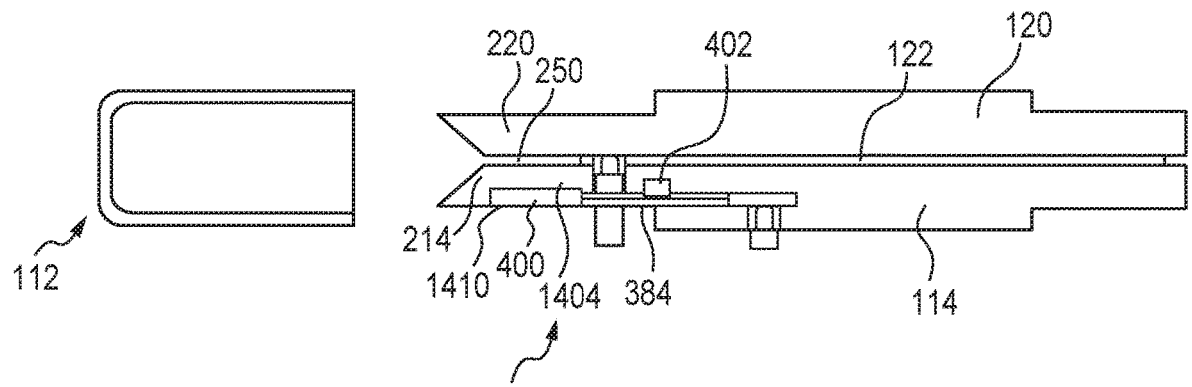
FIG. 25 is a schematic cross-sectional view of the DS sensing apparatus according to another aspect of the present disclosure.

FIG. 25 illustrates an embodiment of the DS sensing apparatus 100 featuring the at least one heater 400 embedded in the first fin 214. The first fin 214 features a recess 1404 configured for receiving the at least one heater 400 such that an exterior surface 1410 of the at least one heater 400 is flush with the first outer surface 254 of the first fin 214. The support 384 extends to the at least one heater 400 from the body 102. The first thermistor 402 is disposed on the support 384, within the body 102.

Figure 26:
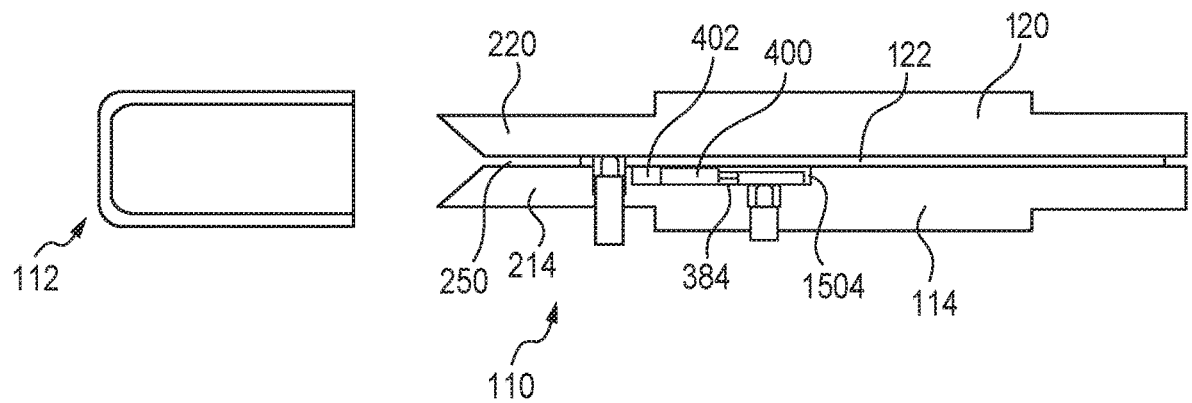
FIG. 26 is a schematic cross-sectional view of the DS sensing apparatus according to another aspect of the present disclosure.

FIG. 26 illustrates an embodiment of the DS sensing apparatus 100 featuring the at least one heater 400 and the first thermistor 402 adjacent to each other, and interposed between the upper body 114 and the spacer 122. The at least one heater 400 is disposed in the body 102, while the first thermistor 402 is disposed in the first fin 214. The at least one heater 400 and the first thermistor 402 are connected to the support 384, which is disposed within the body 102 on an opposite side of the liquid-tight seal (for example provided by the gasket 382) as the test volume 250. Each of the first thermistor 402, the at least one heater 400, and the support 384 are received in an upper body recess 1504 defined in the upper body 114.

Figure 27:
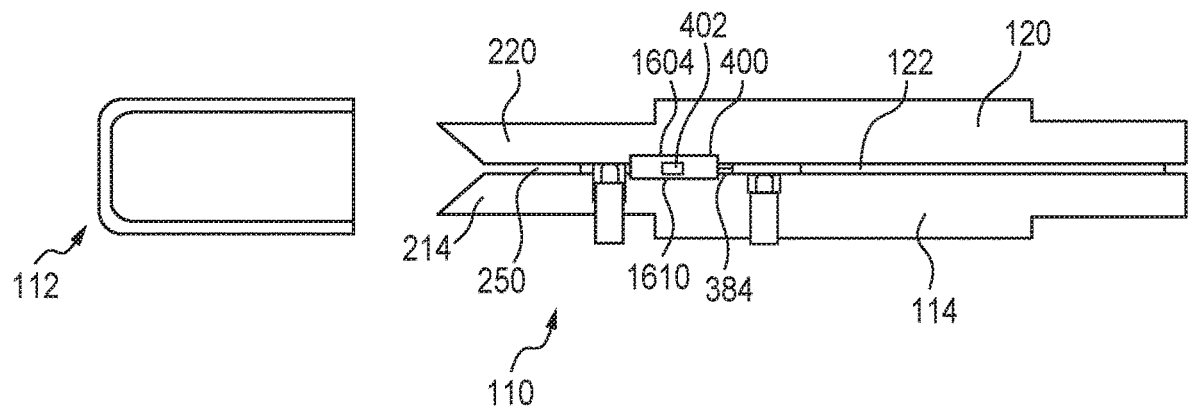
FIG. 27 is a schematic cross-sectional view of the DS sensing apparatus according to another aspect of the present disclosure.

FIG. 27 illustrates an embodiment of the DS sensing apparatus 100 featuring the at least one heater 400 and the first thermistor 402 interposed between the lower body 120 and the upper body 114, within a gap having a depth defined by the spacer 122. The at least one heater 400 and the first thermistor 402 are connected to the support 384, which is disposed within the body 102 on an opposite side of the liquid-tight seal (for example provided by the gasket 382) as the test volume 250. The upper body 114 features an upper body heater cavity 1610 configured for receiving the at least one heater 400, and the lower body 120 features a lower body heater cavity 1604 configured for receiving the at least one heater 400.

Figure 28:
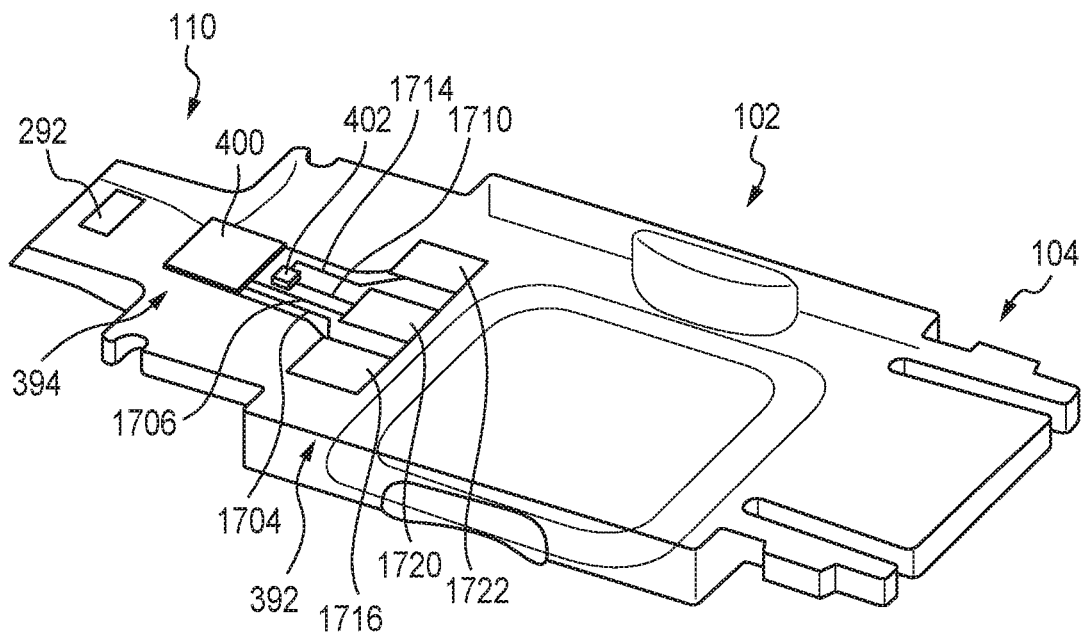
FIG. 28 is a perspective view of the body of the DS sensing apparatus according to another aspect of the present disclosure.
Figure 29:
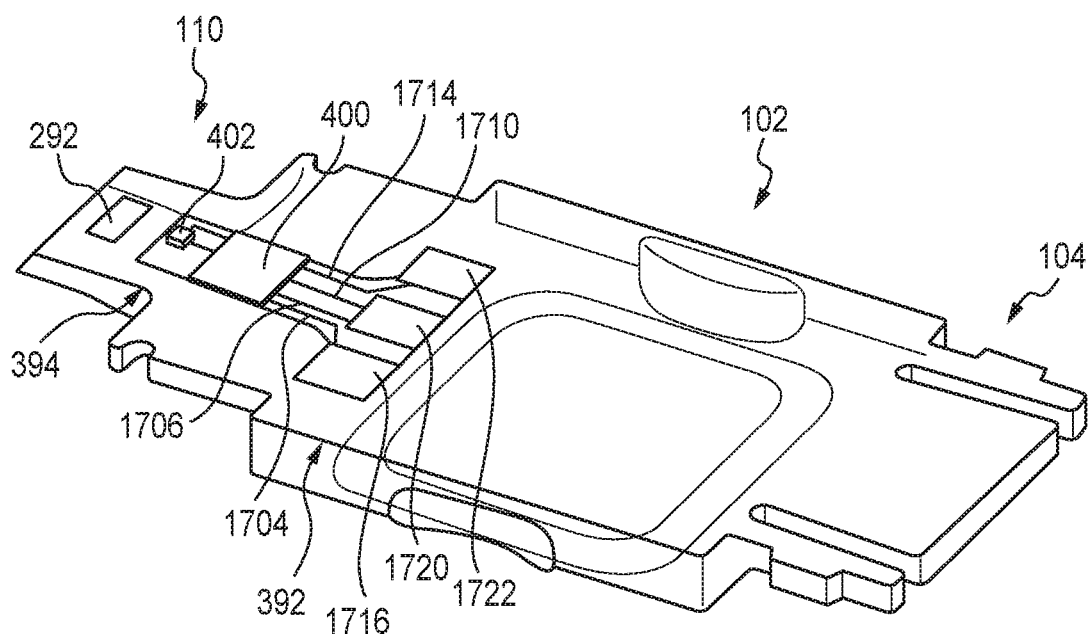
FIG. 29 is a perspective view of the body of the DS sensing apparatus according to another aspect of the present disclosure.
Figure 30:
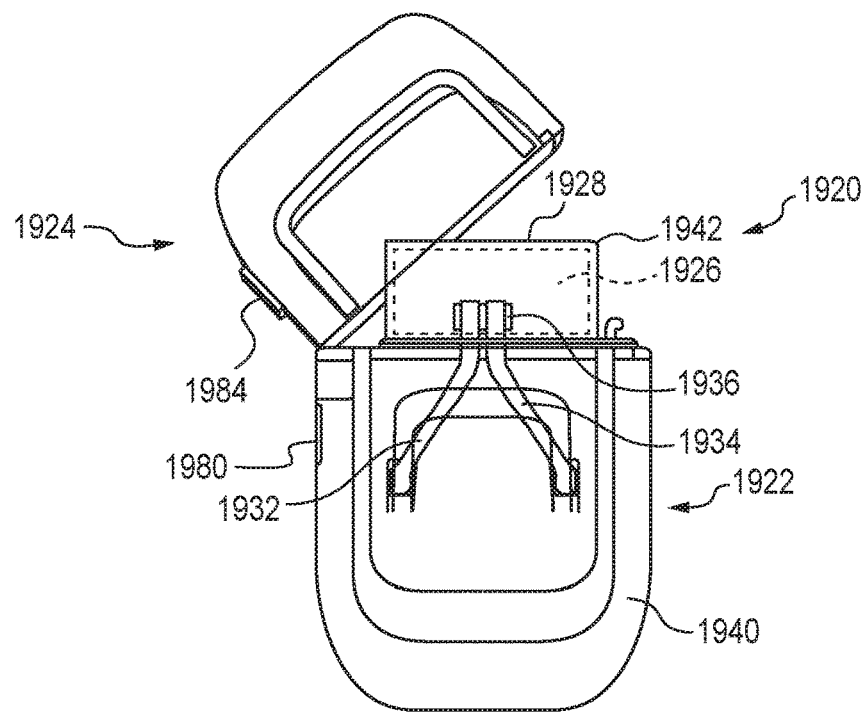
FIG. 30 is a plan view of a DS sensing apparatus according to another aspect of the present disclosure with a lid in an open position.

FIG. 28 illustrates an embodiment of the DS sensing apparatus 100 featuring the at least one heater 400 between the test volume 250 and the first thermistor 402, while FIG. 29 illustrates an embodiment of the DS sensing apparatus 100 featuring the first thermistor 402 disposed between the at least one heater 400 and the test volume 250. In this manner, the first thermistor 402 may be disposed either in front of or behind the at least one heater 400 with respect to the test volume 250. Also, each of FIGS. 28 and 29 illustrate an embodiment of the DS sensing apparatus 100 featuring heating system electrodes 1704, 1706, 1710, 1714 with corresponding contacts 1716, 1720, 1722 aligned in a row, laterally across the body 102. The medial contact 1720 corresponds to both the at least one heater 400 and the first thermistor 402, while the lateral contacts correspond to the at least one heater 400. The conductive insert 404 may be an overmolded copper insert connected to the at least one heater 400 and configured to conduct heat towards the test volume 250. Notably, incorporating the first thermistor 402 into the DS sensing apparatus 100 heating system enables the DS sensing apparatus 100 to receive a temperature data input used to regulate the at least one heater 400, thereby improving accuracy in maintaining the temperature of the sample in the test volume 250 within a desired range.

FIGS. 30-36 depict a DS sensing apparatus 1920 including a body 1922 and a cap 1924 that cooperates with the body 1922. The body 1922 defines a test volume 1926 into which fluid enters from a fluid inlet 1928 via capillary action. Electrodes, or at least portions thereof, reside in the test volume 1926 (see FIG. 30) to allow DS testing to be undertaken on the fluid within the test volume 1926. After the fluid is loaded into the test volume 1926 and the cap 1924 is closed (see FIG. 32), the DS sensing apparatus 1920 is configured to be inserted into an analyzer device (not shown) so that DS testing can be performed on the fluid within the test volume 1926.

The body 1922 and the cap 1924 can be fabricated from poly(methyl methacrylate) (PMMA), also known as acrylic or acrylic glass. Accordingly, the body 1922 and the cap 1924 can be clear, which can allow for visual indication to the user that fluid resides in the test volume 1926 and also provides an indication of the location of the sensing electrodes 1932, 1934 and the floating electrode 1936.

Figure 31:
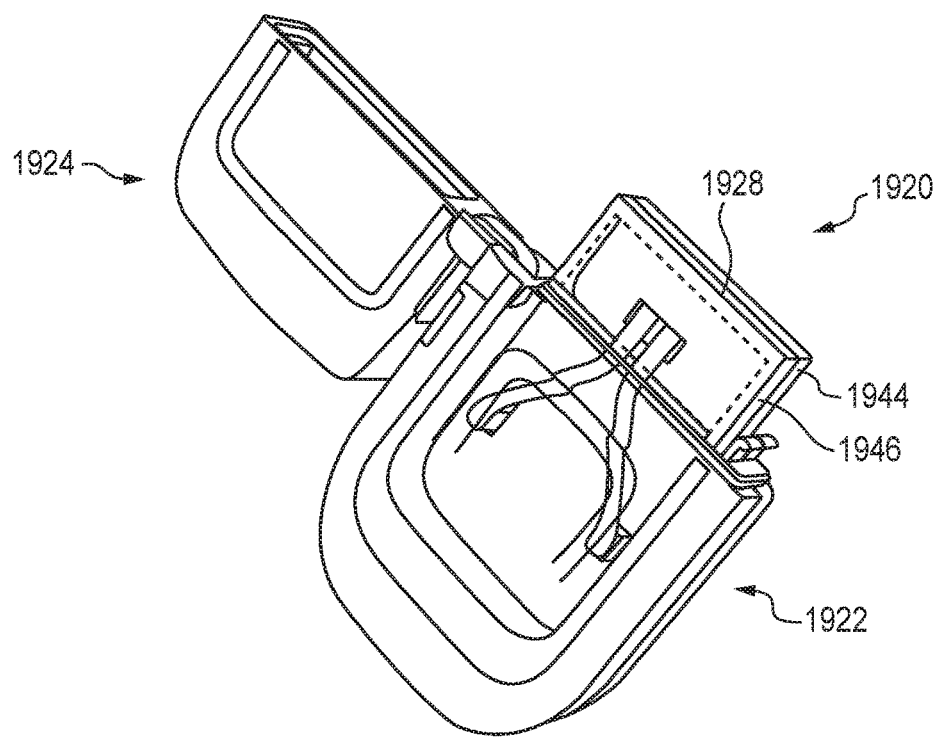
FIG. 31 is a perspective view of the DS sensing apparatus of FIG. 30 with the lid in an open locked position.
Figure 32:
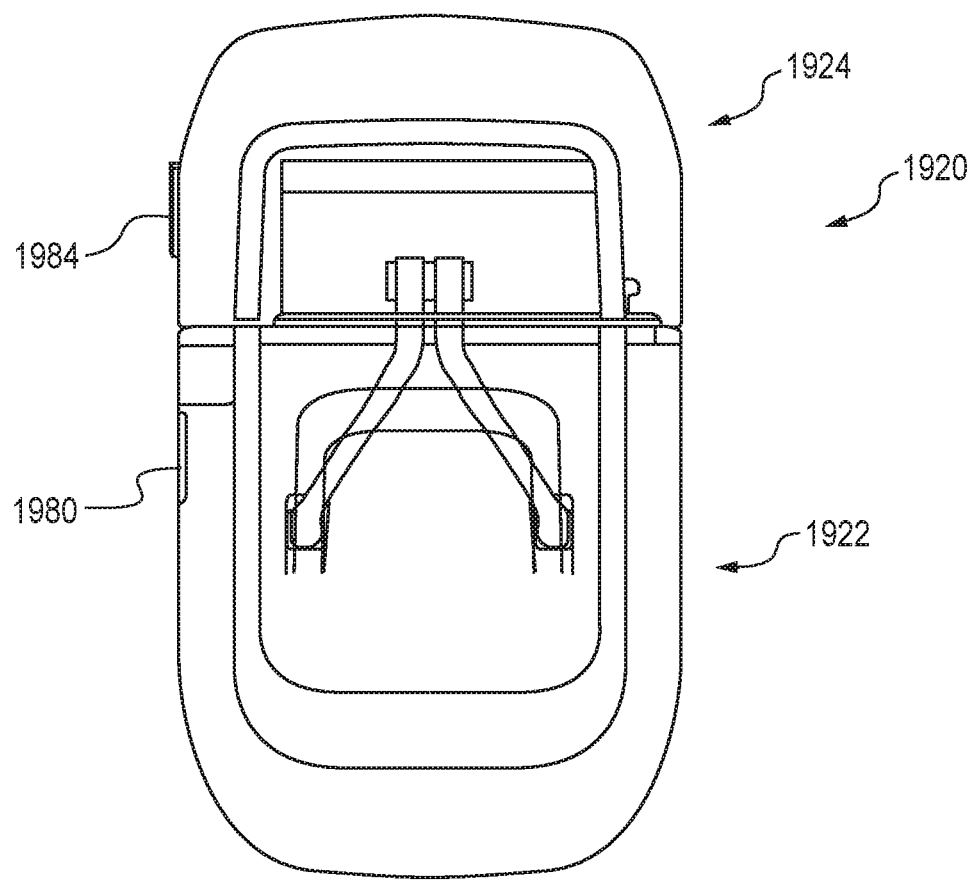
FIG. 32 is a plan view of the DS sensing apparatus of FIG. 30 with the lid in a closed position.
Figure 33:
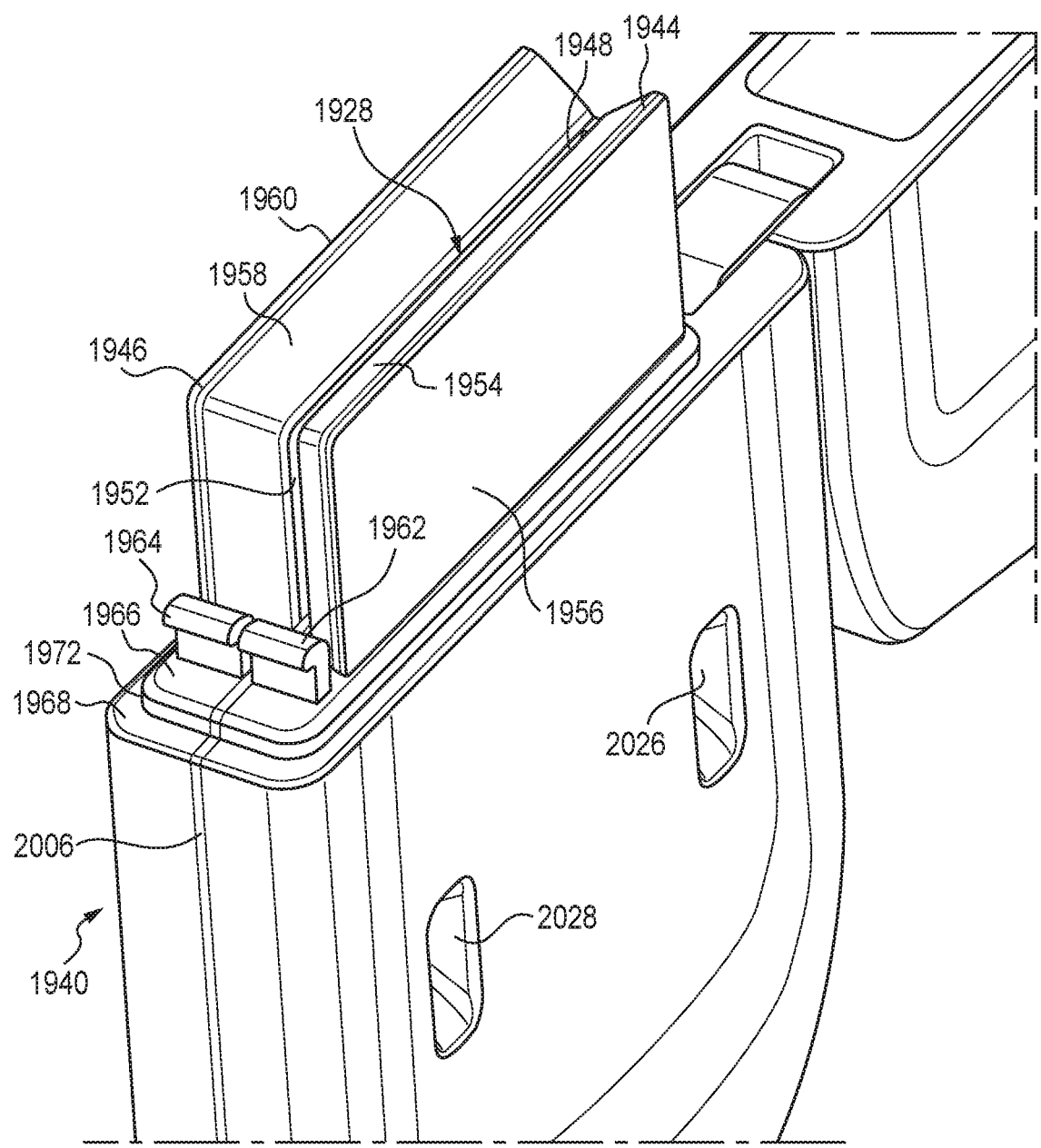
FIG. 33 is a partial perspective view of the DS sensing apparatus of FIG. 30 with the lid in the open locked position.

When finally assembled, the body 1922 includes a base portion 1940 and a cantilever portion 1942 that extends from the base portion 1940. With reference to FIGS. 31 and 32, the cantilever portion 1942 includes a first fin 1944 and a second fin 1946 each extending from the base portion 1940. With particular reference to FIG. 33, which does not show the electrodes 1932, 1934, 1936, the first fin 1944 defines a first inner surface 1948 and the second fin 1946 defines an opposing second inner surface 1952 spaced from the first inner surface 1948. The first inner surface 1948 is spaced from the second inner surface 1952 a distance that allows the fluid to enter the test volume 1926 from the fluid inlet 1928 via capillary action. In the illustrated embodiment, the first inner surface 1948 is planar (flat) and parallel with the second inner surface 1952, which is also planar. The first inner surface 1948 can be spaced from the second inner surface 1952 less than about 500 μm and preferably about 50 μm. The first sensing electrode 1932 and the second sensing electrode 1934 are provided on the first inner surface 1948 and the floating electrode 1936 is provided on the second inner surface 1952 so as to be spaced apart from the sensing electrodes 1932, 1934 within the test volume 1926. The fins 1944, 1946 in the illustrated embodiment are shown as rectangular in plan view, however, the fins 1944, 1946 can take other shapes, e.g., they may have a curved periphery.

The first fin 1944 includes a beveled peripheral edge 1954 that is angled from a first outer surface 1956 toward the base portion 1940 to the first inner surface 1948 and the fluid inlet 1928. The second fin 1946 similarly includes a beveled peripheral edge 1958 that is angled from a second outer surface 1960 toward the base portion 1940 to the second inner surface 1952 and the fluid inlet 1928.

The fluid inlet 1928 in the illustrated embodiment is disposed along a peripheral edge of the test volume 1926. With reference to FIG. 31, the fluid inlet 1928 is L-shaped in plan view. This configuration allows a user of the DS sensing apparatus 1920 to prick his/her skin, for example at one's finger, to deposit a droplet of blood on the beveled peripheral edge 1954, 1958, which will then be drawn into the test volume, which obviates the need for a pipette or dropper to load the test volume 1926 with a fluid to be tested. In the illustrated embodiment, the fluid inlet 1928 is along a linear edge of the test volume 1926 that is spaced farthest from the base portion 1940 and also includes a side peripheral edge extending from the farthest edge of the test volume 1926 and towards the base portion 1940. In the illustrated embodiment, the test volume 1926 is generally rectangular in plan view (see FIG. 30) and the fluid inlet 1928 is located along two adjacent sides of this rectangle. As such, the fluid inlet 1928 is relatively long and nearly equal to the longest dimension of the test volume 1926. In the illustrated embodiment, two sides of the rectangular test volume 1926 are closed, i.e. not open to ambient when the cap 1924 is not placed on the body 1922, however, at least one, e.g. a side parallel to the side extending between the farthest edge and the base portion 1940 can be opened to ambient.

When the fins 1944, 1946 take configurations other than rectangular, the beveled peripheral edges 1954, 1958 can also take configurations other than linear. Indicia, such as frosting on the fins 1944, 1946 to provide opaque or translucent sections, can outline the test volume 1926 and provide a location for a user to target a blood droplet, for example. Also, the profile of each beveled edge can be one of (1) a chamfer, which is shown in FIGS. 30-36, (2) a radius, or (3) a combination of a chamfer and a radius.

The body 1922 further includes cap catches 1962 and 1964 extending away from the base portion 1940 in the same direction that the fins 1944 and 1946 extend from the base portion 1940. Both the fins 1944, 1946 and the cap catches 1962, 1964 extend from a pedestal surface 1966 that is offset from a ledge surface 1968, which defines an edge of the base portion 1940 closest to the cantilever portion 1942. Both the pedestal surface 1966 and the ledge surface 1968 reside in respective planes that are normal to the direction in which the fins 1944, 1946 extend from the base portion 1940. The cap catches 1962, 1964 cooperate with the cap 1924 so as to preclude removal of the cap 1924 from the body 1922 once the cap 1924 has been brought into the closed position, which is shown in FIG. 32. As such, the DS sensing apparatus 1920 can be a "single use" device in that opening the cap 1924 after the cap 1924 has been placed into the closed position shown in FIG. 31 is precluded unless the cap catches 1962, 1964 and/or the cap 1924 are broken. With reference back to FIG. 33, a gasket 1970 can surround a pedestal 1972 (an upper surface of which is the pedestal surface 1966) to cooperate with the cap 1924 when the cap 1924 is in the closed position with respect to the body 1922 so as to preclude fluid from escaping the DS sensing apparatus 1920.

Figure 34:
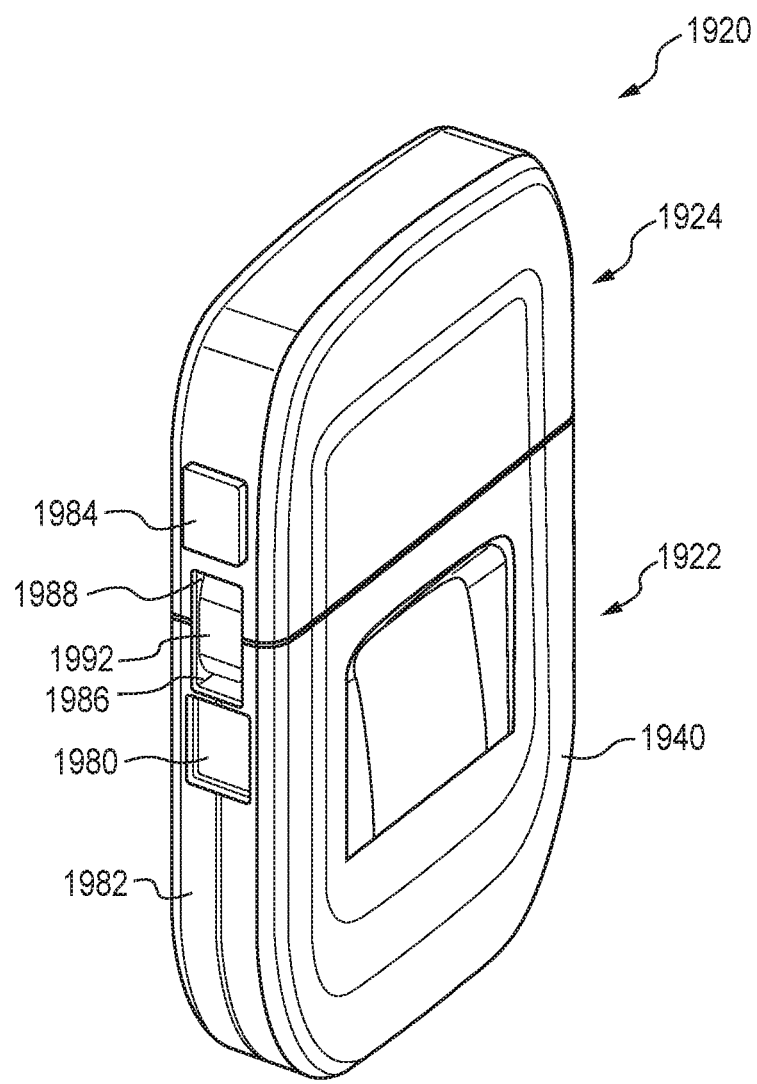
FIG. 34 is a perspective view of the DS sensing apparatus of FIG. 30 with the lid in the closed position.

With reference to FIG. 34, the body 1922 includes a lid connector recess 1980 provided along a peripheral edge 1982 of the body 1922 and more particularly in the base portion 1940 of the body 1922. The lid connector recess 1980 is shaped to receive a corresponding protuberance 1984 provided on the cap 1924 so as to fix the cap 1924 with respect to the body 1922 when the cap 1924 is in the open locked position (see FIG. 31). When in the open locked position, the protuberance 1984 frictionally engages side surfaces of the lid connector recess 1980 when received in the lid connector recess 1980. This fixes the location of the cap 1924 with respect to the body 1922, which facilitates loading the test volume 1926 in that the user need not hold the cap 1924 to inhibit the cap 1924 from moving with respect to the body 1922. The protuberance 1984 is removable from the lid connector recess 1980 by overcoming the frictional force between the protuberance 1984 and the side surfaces of the lid connector recess 1980, which allows pivotal movement of the cap 1924 with respect to the body 1922 (see FIG. 30) to allow the DS sensing apparatus 1920 to move from the open locked position shown in FIG. 31 through the open position shown in FIG. 30 to the closed position shown in FIG. 32.

With continued reference to FIG. 34, the body 1922 includes a hinge connector recess, hereinafter the body hinge connector recess 1986. Similarly, the cap 1924 includes a hinge connector recess, which will be referred to as the cap hinge connector recess 1988. A hinge connector linkage 1992 is received in the body hinge connector recess 1986 and the cap hinge connector recess 1988 and is connected to each of the body 1922 and the cap 1924 to allow for movement of the cap 1924 with respect to the body 1922 from the open position (shown in FIG. 31) to the closed position (shown in FIG. 32). The hinge connector linkage 1992 also allows for some translational movement of the cap 1924 with respect to the body 1922.

Figure 35:
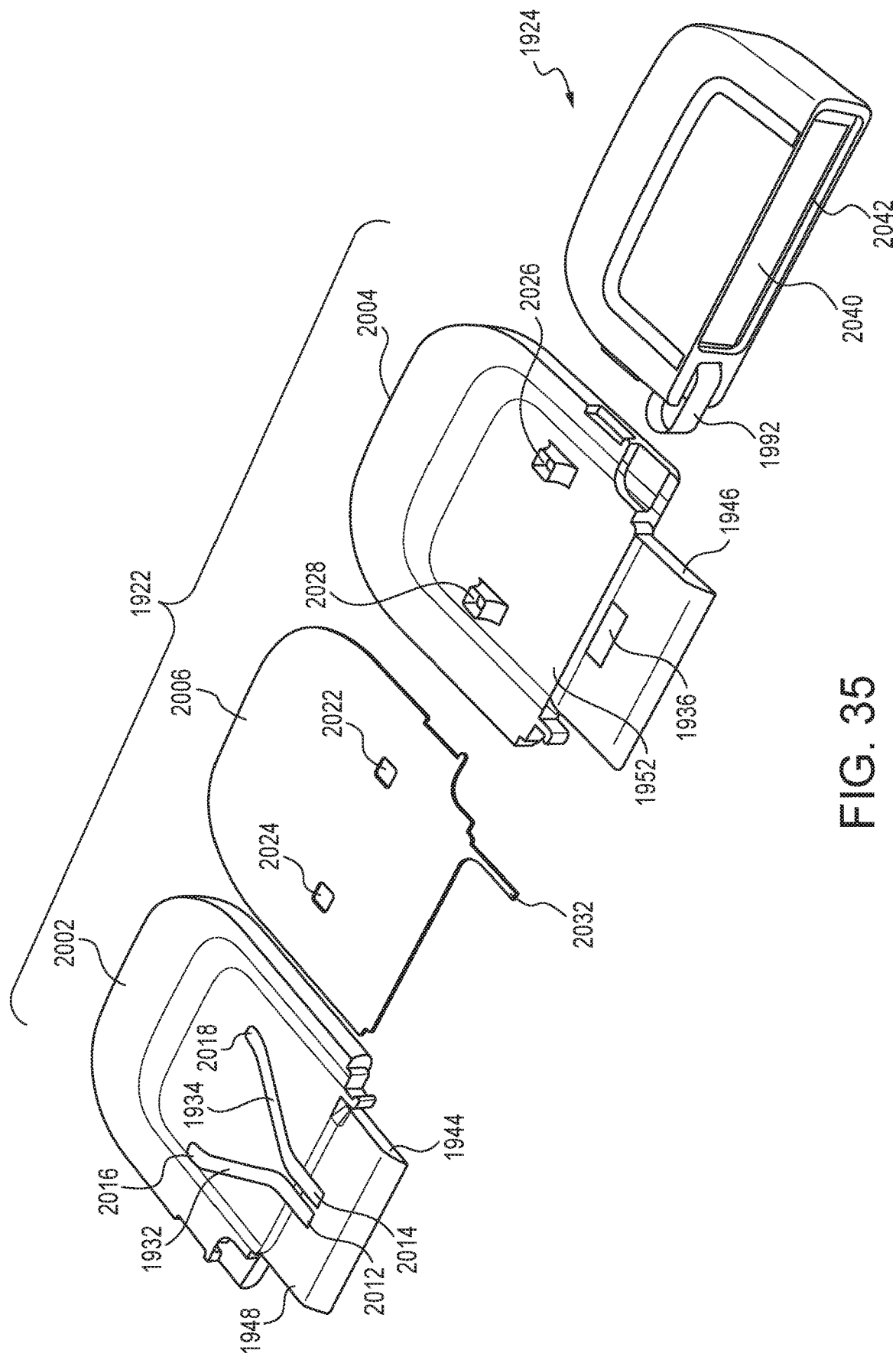
FIG. 35 is an exploded perspective view of the DS sensing apparatus of FIG. 30.

FIG. 35 depicts an exploded view of the body 1922, which can be made up of a first (top) part 2002, a second (bottom) part 2004, and a spacer 2006 interposed between the top part 2002 and the bottom part 2004 (see FIG. 33). The spacer 2006 can be a double-sided adhesive tape that is used to connect to the top part 2002 with the bottom part 2004 and to provide the appropriate spacing between the first inner surface 1948 and the second inner surface 1952 to provide for the test volume 1926. The spacer 2006 could also be made from poly(methyl methacrylate) (PMMA) and an adhesive could be applied to the opposing surfaces to allow for the attachment of the top part 2002 to the bottom part 2004.

Each of the sensing electrodes 1932, 1934 are provided on the top part 2002 and extend from a respective first terminal end 2012, 2014 located on the first inner surface 1948 within the test volume 1926 on the first fin 1944 into the base portion 1940 to a respective second terminal end 2016, 2018 that is located within the base portion 1940. The sensing electrodes 1932, 1934 are deposited along, e.g. printed, the first inner surface 1948 in such a manner that when covered by the spacer 2006, which has adhesive deposited thereon, with the bottom part 2004 also adhered to the spacer 2006, fluid in the test volume 1926 is precluded from traveling beyond the pedestal surface 1966 towards the second terminal ends 2016, 2018 of the respective sensing electrodes 1932, 1934. The floating electrode 1936 is provided on the second inner surface 1952 on the bottom part 2004. Each of the sensing electrodes 1932, 1934 and the floating electrode 1936 can be an electrically conductive material (e.g., gold, copper or aluminum) deposited on the appropriate surface by, for example, sputter deposition using a shadow mask and lift-off process. As an example, each of the sensing electrodes 1932, 1934 and the floating electrode 1936 can be formed with a thickness of 1000 angstroms or less.

The spacer 2006 includes pin openings 2022, 2024 that align with the respective second terminal ends 2016, 2018 of the sensing electrodes 1932, 1934 when the spacer 2006 is appropriately positioned on the first inner surface 1948 of the base portion 1940 of the top part 2002. Similarly, the bottom part 2004 includes pin openings 2026, 2028 which align with the pin openings 2022, 2024, respectively, in the spacer 2006 when the spacer 2006 is appropriately positioned on the top part 2002 and the bottom part 2004 is appropriately positioned on the spacer 2006. Connector or pogo pins can extend through the openings 2022, 2026 and the openings 2024, 2028 to provide for an electrical connection with the second terminal ends 2016, 2018 of the respective sensing electrodes 1932, 1934 to provide the appropriate input and output RF signals to the sensing electrodes 1932, 1934, which is described in more detail in U.S. Pat. No. 9,995,701 B2.

The spacer 2006, which has been described above as an adhesive tape, has a peripheral edge that matches the peripheral edge of the top part 2002 and the bottom part 2004 in the base portion 1940. Little, if any, of the spacer 2006 extends into the cantilever portion 1942 of the body 1922. The spacer 2006 may, however, include a finger-like extension 2032 that extends into the cantilever portion along one edge of each fin 1944, 1946. As such, as described above the fluid inlet 1928 may only be on two edges of each rectangular fin 1944, 1946 because of the location of the finger-like extension 2032. With reference to FIG. 33, with the exception of the finger-like extension 2032, the periphery of the spacer 2006 terminates so as to be co-planar with the pedestal surface 1966 and the ledge surface 1968 such that one edge of the spacer 2006 is co-planar with the pedestal surface 1966, which defines one edge of the test volume 1926.

Figure 36:
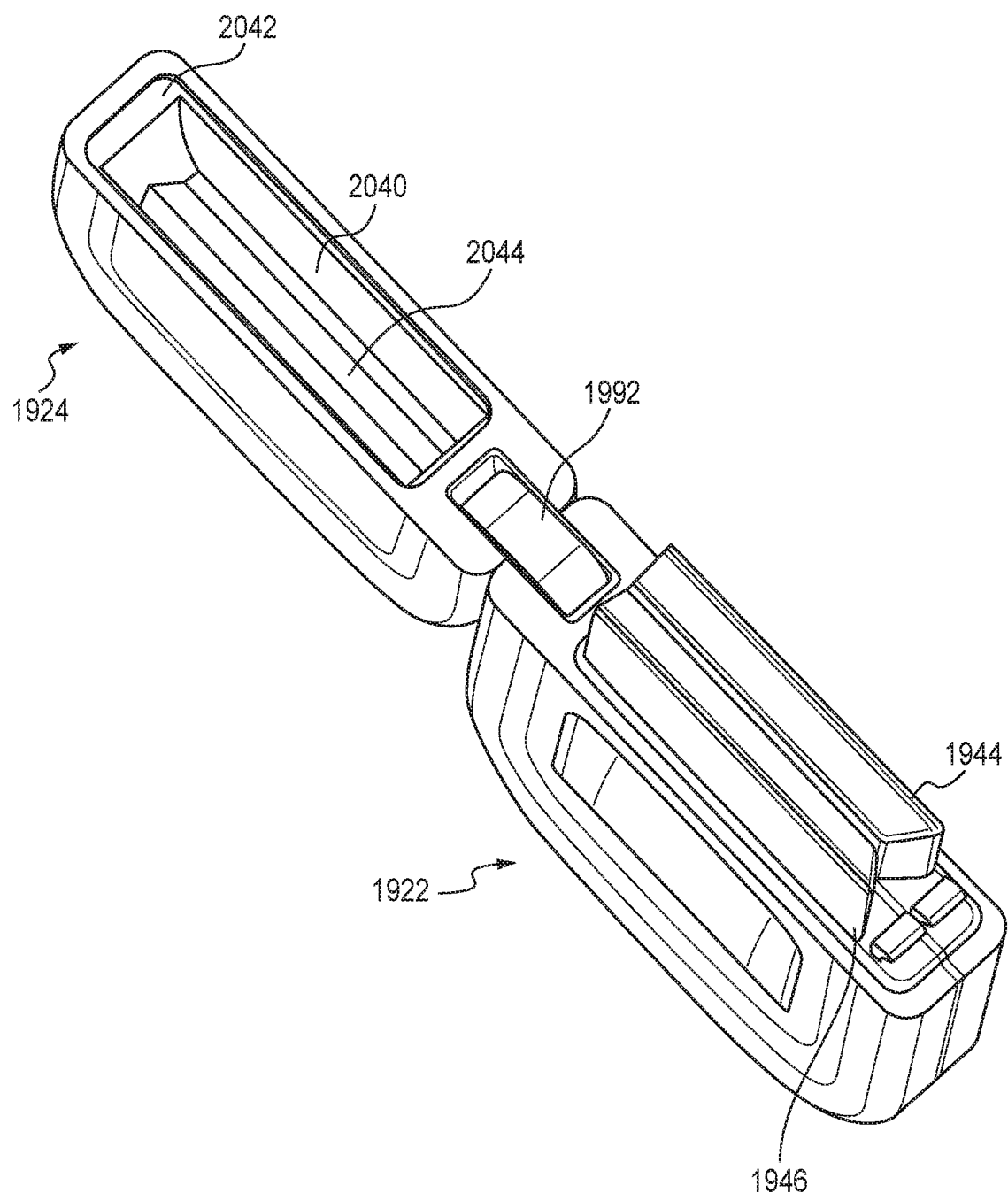
FIG. 36 is a perspective view of the DS sensing apparatus of FIG. 30 with the lid in the open locked position.

The cap 1924 is hinged to the body 1922 via the hinge connector linkage 1992. The hinge connector linkage 1992 can connect with the cap 1924 and the body 1922 in a manner that allows both pivotal and translational movement of the cap 1924 with respect to the body 1922. The cap 1924 includes a receptacle 2040 in which the cantilever portion 1942 of the body 1922 is received when the cap 1924 is in the closed position (see FIG. 32). The cap 1924 can also include a recessed ledge 2042 that is similar and in configuration to the pedestal 1972 so as to cooperate with the gasket 1970, should one be provided. When the cap 1924 is in the closed position, the fluid within the test volume 1926 is sealed from ambient so as to preclude evaporation of the fluid therein for at least 30 minutes so that DS testing can be performed. With particular reference to FIG. 36, an angled protrusion 2044 provided in the cap 1924 can cooperate with the fins 1944, 1946, and more particularly the beveled peripheral edges 1954, 1958 of the fins 1944, 1946 to maintain desired spacing between first inner surface 1948 and the second inner surface 1952 while DS testing is being performed on the fluid within the test volume 1926. The angled surfaces of the angled protrusion 2044 can match the angled surfaces of the beveled peripheral edges 1954, 1958.

In use, the DS sensing apparatus 1920 can be packaged with the cap 1924 in the open locked position shown in FIGS. 31 and 33. A droplet of fluid, e.g., blood, can be deposited on the beveled peripheral edges 1954, 1958 directly from a user's finger, for example. The droplet of fluid is then drawn through the fluid inlet 1928 into the test volume 1926 via capillary action without the need for a wicking element. The cap 1924 is then closed (FIG. 32) and the DS sensing apparatus 1920 can be loaded into an analyzer device (not shown) where pogo pins, for example, are in contact with the respective second terminal ends 2016, 2018.

It will be appreciated that variations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A dielectric spectroscopy (DS) sensing apparatus comprising:

a body defining a test volume between a first surface and an opposing second surface spaced from the first surface a distance that allows a fluid to enter the test volume from a fluid inlet, which is communicatively coupled with the test volume, via capillary action, wherein the body comprises a first body end portion and a second body end portion;

electrodes provided on the body including a first sensing electrode on the first surface and configured to receive an input radio frequency (RF) signal, a second sensing electrode on the first surface spaced from the first sensing electrode and configured to deliver an output RF signal, and a floating electrode on the second surface; and a cap configured to connect with the first body end portion and the second body end portion.

2. The DS sensing apparatus of claim 1, wherein the cap is removable from the first body end portion when the cap is connected with the first body end portion so as not to damage the cap or body, and the cap is not removable from the second body end portion when the cap is connected with the second body end portion, such that removal of the cap from the second body end portion after the cap has been connected with the second body end portion will result in damage to the cap or body.

3. The DS sensing apparatus of claim 2, further comprising:

at least one locking mechanism extending from the second body end portion, wherein the cap includes at least one corresponding notch configured to engage the at least one locking mechanism when the cap engages the second body end portion, wherein, the cap is locked onto the second body end portion such that the cap cannot be removed from the second end without damaging some portion of the DS sensing apparatus when the at least one locking mechanism has engaged the at least one notch.

4. The DS sensing apparatus of claim 1, further comprising:

at least one protuberance extending from the first body end portion, the at least one protuberance being configured to connect with the cap in a fixed position with respect to the first body end portion, and the cap includes at least one recess configured for receiving the at least one protuberance in the fixed position, wherein the at least one protuberance is configured to be maneuvered so as to remove the at least one protuberance from the at least one recess, thereby releasing the cap from the fixed position with the first body end portion.

5. The DS sensing apparatus of claim 1, further comprising a gasket disposed around the periphery of the second body end portion, and wherein the gasket and the cap form a liquid-tight seal when the cap is connected with the second body end portion.

6. The DS sensing apparatus of claim 1, wherein the cap is at least one of reversible with respect to the first end portion such that the cap may engage the first end portion in two orientations distinguished by a 180 degree rotation of the cap with respect to the first end portion, and reversible with respect to the second end portion such that the cap may engage the second end portion in two orientations distinguished by a 180 degree rotation of the cap with respect to the second end portion.

7. The DS sensing apparatus of claim 1, further comprising a gasket disposed around the periphery of the second body end portion, and wherein the gasket and the cap form a liquid-tight seal when the cap is connected with the second body end portion, wherein the second body end portion comprises pin openings, and the gasket is located between the pin openings and the test volume.

8. The DS sensing apparatus of claim 1, wherein the cap comprises pin holes defined on a first cap side, and pin holes defined on a second cap side, and
Wherein the pin holes on the first cap side are coaxial with the pin holes on the second cap side.

9. The DS sensing apparatus of claim 1, wherein the body is formed from an upper body and a lower body with the test volume defined by a first fin extending from the upper body and a second fin extending from the lower body, and the body further comprises an insert forming at least a portion of the first fin, the insert having at least one of the first sensing electrode and the second sensing electrode disposed thereon.

10. The DS sensing apparatus of claim 1, wherein the body is formed from an upper body and a lower body with the test volume defined by a first fin extending from the upper body and a second fin extending from the lower body, and the body further comprises an insert forming at least a portion of the second fin, the insert having the floating electrode disposed thereon.

11. A dielectric spectroscopy (DS) sensing apparatus comprising:
    a body defining a test volume between a first surface and an opposing second surface spaced from the first surface a distance that allows a fluid to enter the test volume from a fluid inlet, which is communicatively coupled with the test volume, via capillary action; and
    electrodes provided on the body including a first sensing electrode on the first surface and configured to receive an input radio frequency (RF) signal, a second sensing electrode on the first surface spaced from the first sensing electrode and configured to deliver an output RF signal, and a floating electrode on the second surface, wherein the first sensing electrode includes a first terminal end and a second terminal end, the second sensing electrode includes a first terminal end and a second terminal end,
    wherein the body defines pin openings positioned to expose the second terminal end of the first sensing electrode and the second terminal end of the second sensing electrode to an exterior of the DS sensing apparatus such that the second terminal end of the first sensing electrode and the second terminal end of the second sensing electrode are accessible to an analyzer device, and
    wherein the pin openings are positioned on an opposite side of a liquid-tight seal as compared to the test volume.

12. A dielectric spectroscopy (DS) sensing apparatus comprising:
    a body defining a test volume between a first surface and an opposing second surface spaced from the first surface a distance that allows a fluid to enter the test volume from a fluid inlet, which is communicatively coupled with the test volume, via capillary action; and
    electrodes provided on the body including a first sensing electrode on the first surface and configured to receive an input radio frequency (RF) signal, a second sensing electrode on the first surface spaced from the first sensing electrode and configured to deliver an output RF signal, and a floating electrode on the second surface,
    wherein the body includes a first end portion and a second end portion, and the fluid inlet is defined by a cantilever portion extending from the body as part of the second body end portion, the cantilever portion including a first fin and a second fin,
    wherein the first fin extends the first surface from the body, and the second fin extends the second surface from the body, and
    wherein the second body end portion includes a neck down portion defined by a pedestal surface on the second body end portion and the fluid inlet.

13. A dielectric spectroscopy (DS) sensing apparatus comprising:
    a body defining a test volume between a first surface and an opposing second surface spaced from the first surface a distance that allows a fluid to enter the test volume from a fluid inlet, which is communicatively coupled with the test volume, via capillary action;
    electrodes provided on the body including a first sensing electrode on the first surface and configured to receive an input radio frequency (RF) signal, a second sensing electrode on the first surface spaced from the first sensing electrode and configured to deliver an output RF signal, and a floating electrode on the second surface; and
    a heater, wherein the heater is positioned on an opposite side of a liquid-tight seal as compared to the test volume so as to preclude liquid from contacting the heater.

14. A dielectric spectroscopy (DS) sensing apparatus comprising:
    a body defining a test volume between a first surface and an opposing second surface spaced from the first surface a distance that allows a fluid to enter the test volume from a fluid inlet, which is communicatively coupled with the test volume, via capillary action; and
    electrodes provided on the body including a first sensing electrode on the first surface and configured to receive an input radio frequency (RF) signal, a second sensing electrode on the first surface spaced from the first sensing electrode and configured to deliver an output RF signal, and a floating electrode on the second surface; and
    a heater, wherein the body is formed from an upper body portion and a lower body portion and the heater is disposed on a support that is one of a printed circuit board interposed between the upper body and the lower body, and a flex circuit interposed between the upper body and the lower body, disposed over a raised portion of at least one of the upper body and lower body, and received in a cavity formed in the other of the upper body and the lower body.

15. The DS sensing apparatus of claim 14, wherein the support is a flex circuit, the test volume is defined by a first fin extending from the upper body and a second fin extending from the lower body, an insert forms at least a portion of the first fin, and the flex circuit is disposed between the insert and one of the lower body and upper body such that the flex circuit is separated from the fluid inlet by the insert.

16. The DS sensing apparatus of claim 15, further comprising at least one ridge extending from the insert that is configured for spacing the insert from the flex circuit and accommodating the heater.

17. The DS sensing apparatus of claim 14, further comprising a thermistor disposed on the support with the heater.

18. The DS sensing apparatus of claim 14, wherein the body comprises a first body end portion and a second body end portion, the support further comprises a first support end portion disposed toward the first body end portion, a second support end portion disposed toward the second body end portion, the first support end portion includes electrode contacts disposed thereon, and the heater is disposed on the second end portion of the support.

\* \* \* \* \*